United States Patent
Sugizaki et al.

(10) Patent No.: US 11,346,783 B2
(45) Date of Patent: May 31, 2022

(54) CHEMICAL SENSOR KIT AND ANALYSIS METHOD

(71) Applicant: KABUSHIKI KAISHA TOSHIBA, Minato-ku (JP)

(72) Inventors: Yoshiaki Sugizaki, Kanagawa (JP); Atsunobu Isobayashi, Kanagawa (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 279 days.

(21) Appl. No.: 16/352,431

(22) Filed: Mar. 13, 2019

(65) Prior Publication Data

US 2020/0088641 A1 Mar. 19, 2020

(30) Foreign Application Priority Data

Sep. 14, 2018 (JP) .............................. JP2018-172386

(51) Int. Cl.
*G01N 21/64* (2006.01)
*G01N 33/542* (2006.01)

(52) U.S. Cl.
CPC ....... *G01N 21/6428* (2013.01); *G01N 33/542* (2013.01); *G01N 2021/6439* (2013.01)

(58) Field of Classification Search
CPC ............. G01N 21/6428; G01N 33/542; G01N 2021/6439
See application file for complete search history.

(56) References Cited

U.S. PATENT DOCUMENTS

| | | | |
|---|---|---|---|
| 2011/0039256 A1* | 2/2011 | McGiven ............. | G01N 33/542 435/5 |
| 2013/0095508 A1* | 4/2013 | Campitelli ............ | B01L 3/0217 435/7.94 |
| 2015/0141267 A1 | 5/2015 | Rothberg et al. | |
| 2015/0141268 A1 | 5/2015 | Rothberg et al. | |
| 2015/0177150 A1 | 6/2015 | Rothberg et al. | |
| 2017/0261500 A1 | 9/2017 | Spigone et al. | |
| 2017/0341077 A1* | 11/2017 | Neethirajan ....... | G01N 33/5308 |
| 2018/0275084 A1 | 9/2018 | Saito et al. | |

FOREIGN PATENT DOCUMENTS

| | | |
|---|---|---|
| JP | 5462219 B2 | 4/2014 |
| JP | 2016-537999 A | 12/2016 |
| JP | 2017-502310 A | 1/2017 |
| JP | 2017-529533 A | 10/2017 |
| JP | 2018-163146 A | 10/2018 |

OTHER PUBLICATIONS

June et al. "A Graphene Oxide Based Immuno-biosensor for Pathogen Detection" (Angew Chem Int Ed. 2010 49:5708-5711). (Year: 2010).*
Stoddart et al. Review Article "Fluorescence and Bioluminescence based Approaches to Study GPCR Ligand Binding" (British J. Pharmacology 2016 173:3028-3037). (Year: 2016).*
Valanne et al. "Multiple Sixed Europium (III) chelate-dyed Polystyrene Particles as Donors in FRET—an Application for Sensitive Protein Quantification Utilization Competitive Adsorption" Analyst 2009 134:980-986 (Year: 2009).*
Tian et al. "Graphene and Graphene-like Two-Denominational Materials Based Fluorescence Resonance Energy Transfer (FRET) Assays for Biological Applications" Biosensor and Bioelectronics 2017 89: 123-135 (Year: 2017).*
Sasmal et al. (J. Am. Chem. Soc. 2014 vol. 136, p. 12998-13005) (Year: 2014).*
CN107488583 Chinese Patent Publication (Year: 2017).*
CN107488709 Chinese Patent Publication (Year: 2017).*
CN 107488583 English Translation (Year: 2017).*
CN 107488709 English Translation (Year: 2017).*
Huang Scientific Reports Jan. 2017 p. 1-7 (Year: 2017).*
Yuko Ueno; "On-chip Graphene Biosensor"; NTT Technical Review (vol. 14, No. 8), Aug. 2015, pp. 1-5.
Yuko Ueno et al.; "On-chip graphene oxide aptasensor for multiple protein detection", Analytica Chimica Acta (vol. 866), Oct. 31, 2014, pp. 1-9.
Yuko Ueno "On-chip Braphene Biosensor"; NTT Technical Review (vol. 14. No. 6) Aug. 2015, pp. 1-5.
Yuko Ueno et al.: "Molecular design for enhanced sensitivity of a FRET aptasensor built on the graphene oxide surface": Chemical Communications (vol. 49, No. 88), 2013, pp. 10346-10348.
Yuko Ueno et al.; "On-chip graphene oxide aptasensor for multiple protein detection", Analytica Chimica Acta (vol. 666), Oct. 31, 2014, pp. 1-9.

* cited by examiner

*Primary Examiner* — Changhwa J Cheu
(74) *Attorney, Agent, or Firm* — Oblon, McClelland, Maier & Neustadt, L.L.P.

(57) ABSTRACT

According to one embodiment, a chemical sensor kit includes a chemical sensor and a reagent. The chemical sensor includes a substrate and a channel which includes hexagonal crystal lattices composed of carbon atoms which are arranged on a surface of the substrate. A first substance is fixed to the channel. The reagent includes a second substance labeled with a fluorescent dye. Either one of the first substance or the second substance is a capturing body that has a specific binding ability to a target substance. And the other is a competing substance which has a binding ability to the capturing body and competes with the target substance for binding to the capturing body.

19 Claims, 27 Drawing Sheets

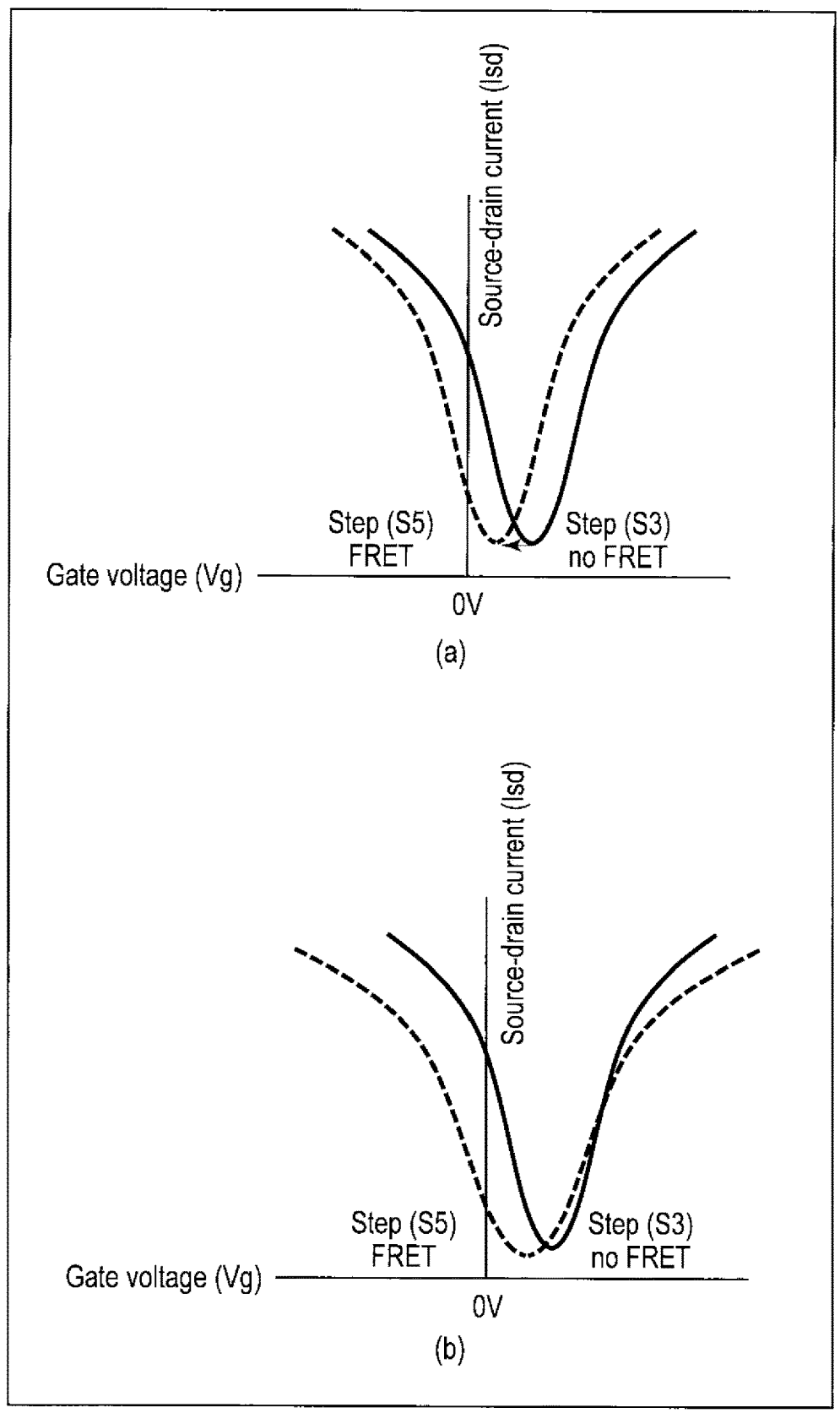
F I G. 10

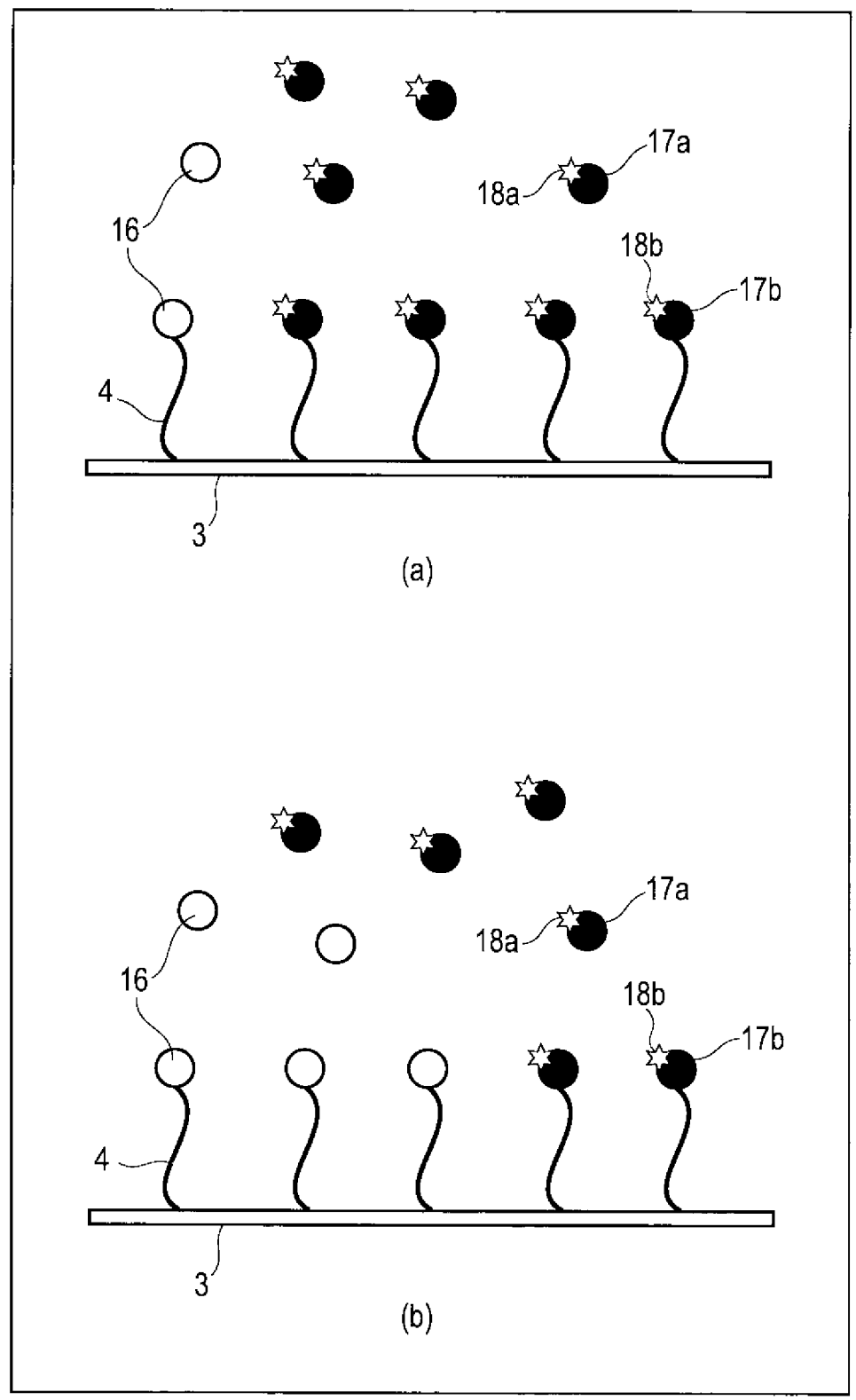
F I G. 12

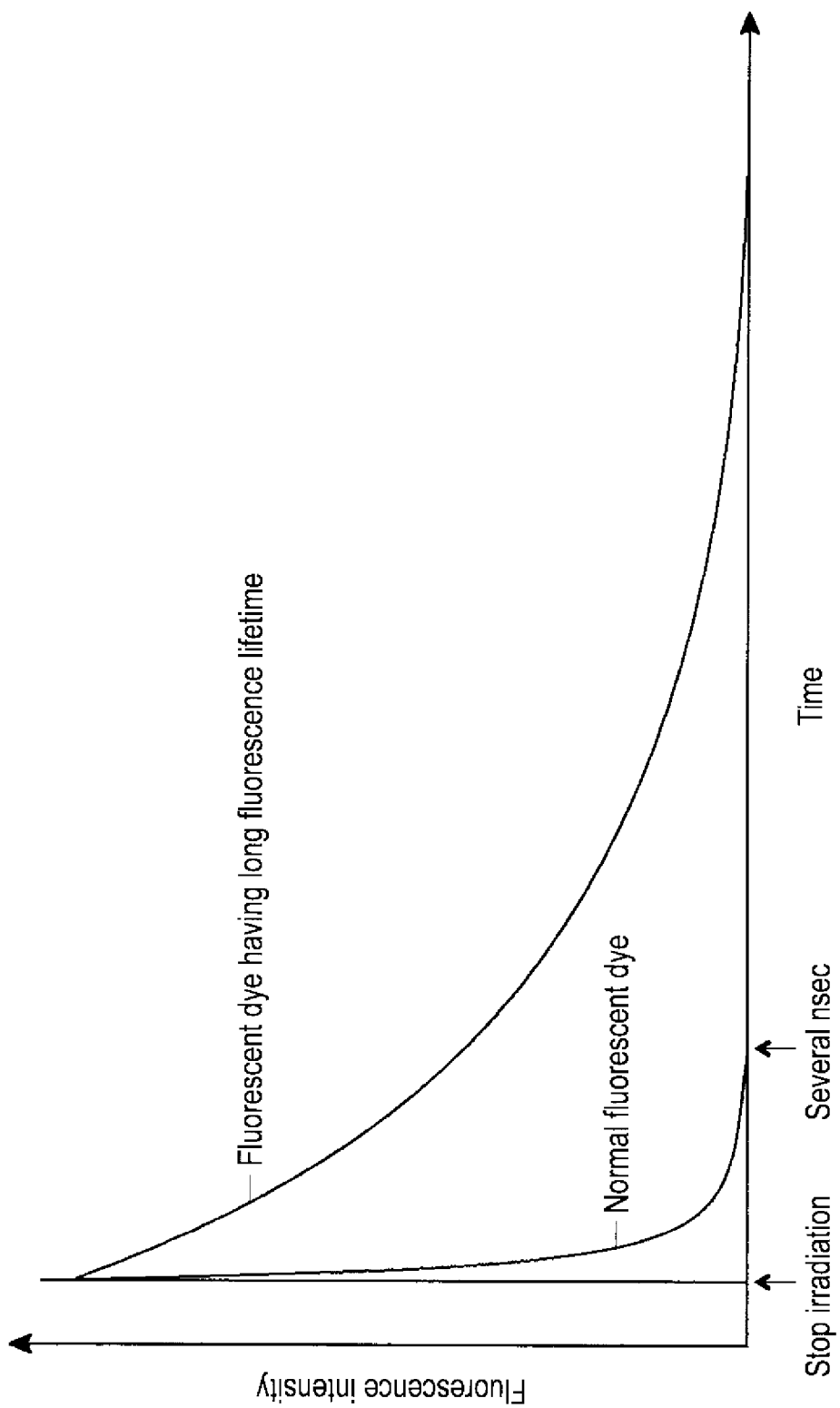
F I G. 17

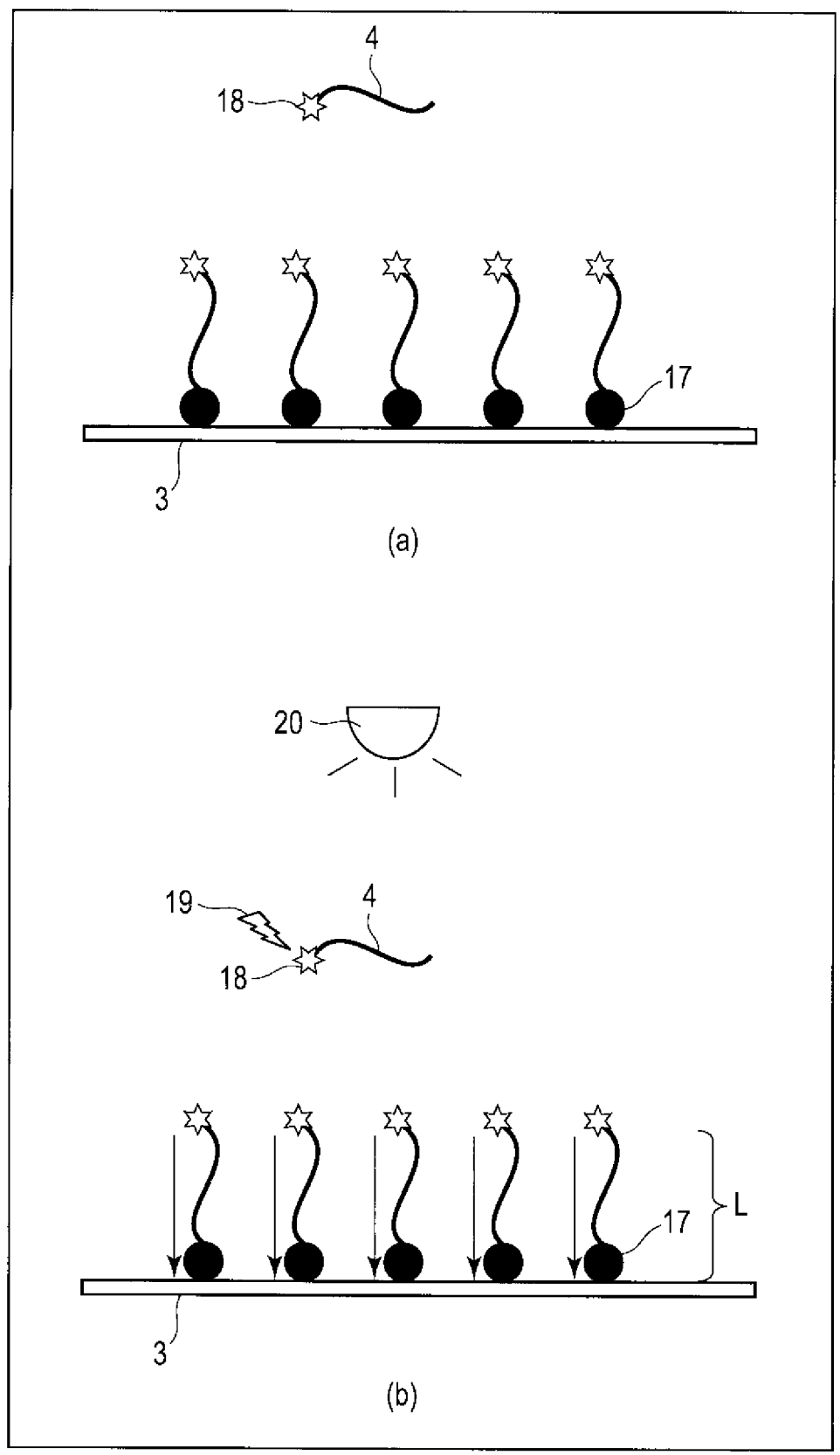
F I G. 21

(a) When concentration of target substance is low (b) When concentration of target substance is high

_US 11,346,783 B2_

CHEMICAL SENSOR KIT AND ANALYSIS METHOD

CROSS-REFERENCE TO RELATED APPLICATIONS

This application is based upon and claims the benefit of priority from Japanese Patent Application No. 2018-172386, filed Sep. 14, 2018, the entire contents of which are incorporated herein by reference.

FIELD

Embodiments described herein relate generally to a chemical sensor kit and an analysis method.

BACKGROUND

A graphene or carbon nanotube is known to function as a quencher of fluorescence. That is, when a fluorescent dye is excited around the graphene or carbon nanotube, excited energy moves to the graphene or carbon nanotube by Fluorescence resonance energy transfer (FRET). Since the graphene or carbon nanotube does not have fluorescence characteristics, the transferred energy is not converted into the fluorescence. Accordingly, the fluorescence of the fluorescent dye is quenched or dimmed.

A method of analyzing a biological substance using above property is disclosed. This method uses a graphene film to which a fluorescent dye-labeled aptamer is fixed.

Under a condition in which a target substance does not exist, the aptamer is stuck to a graphene film surface due to an interaction between a π binding of the aptamer and a π binding of the graphene. Accordingly, FRET is generated between the graphene film and the fluorescent dye, and the fluorescence is quenched or dimmed. On the other hand, under a condition in which the target substance exists, the target substance binds to the aptamer. Thus, the interaction between the π bindings is eliminated, and the aptamer rises. As a result, the fluorescent dye moves away from the graphene film, and thus, the FRET is eliminated, and the fluorescence increases. By observing the increase in the fluorescence by a microscope, the existence of the target substance can be detected.

BRIEF DESCRIPTION OF THE DRAWINGS

FIG. 10 shows graphs of a relationship between $V_g$ and $I_{sd}$.

FIG. 12 shows enlarged diagrams of a state when the chemical sensor of the embodiment is used.

FIG. 17 shows a graph of an example of a relationship between a fluorescence intensity of a fluorescent dye and a time.

FIG. 21 shows enlarged diagrams of the state when the chemical sensor of the embodiment is used.

DETAILED DESCRIPTION

In general, according to one embodiment, a chemical sensor kit includes a chemical sensor and a reagent. The chemical sensor includes a substrate, a channel which includes hexagonal crystal lattices composed of carbon atoms which are arranged on a surface of the substrate, and a first substance which is fixed to the channel. The reagent includes a second substance labeled with a fluorescent dye. Either one of the first substance or the second substance is a capturing body which has a specific binding ability to a target substance. And the other is a competing substance which has a binding ability to the capturing body and competes with the target substance for binding to the capturing body.

Hereinafter, various embodiments will be described with reference to the drawings. Respective drawings are schematic views for the embodiments and understandings thereof, shapes, dimensions, and ratios thereof are different from actual those. However, designs of the embodiments can be appropriately changed with reference to the following descriptions and known techniques.

A chemical sensor kit according to the embodiment is a kit for detecting a target substance in a sample, and includes a chemical sensor and a reagent. The chemical sensor includes a substrate and a channel which includes hexagonal crystal lattices composed of carbon atoms which are arranged on a surface of the substrate. A first substance is fixed to the channel. The reagent includes a second substance labeled with a fluorescent dye.

In a first embodiment, the first substance is a capturing body which has a specific binding ability to a target substance. And the second substance is a competing substance which has a binding ability to the capturing body and competes with the target substance for binding to the capturing body.

In a second embodiment, the second substance is a capturing body which has a specific binding ability to the target substance. And the first substance is a competing substance which has a binding ability to the capturing body and competes with the target substance for the binding to the capturing body.

In a third embodiment, the first substance is a first capturing body that has a specific binding ability to the target substance, and the second substance is a second capturing body which has a specific binding ability to the target substance.

Hereinafter, the first to third embodiments will be described in detail.

First Embodiment

1. Chemical Sensor Kit

A chemical sensor kit of the first embodiment includes a chemical sensor and a reagent.

(1) Chemical Sensor

Figure 1:
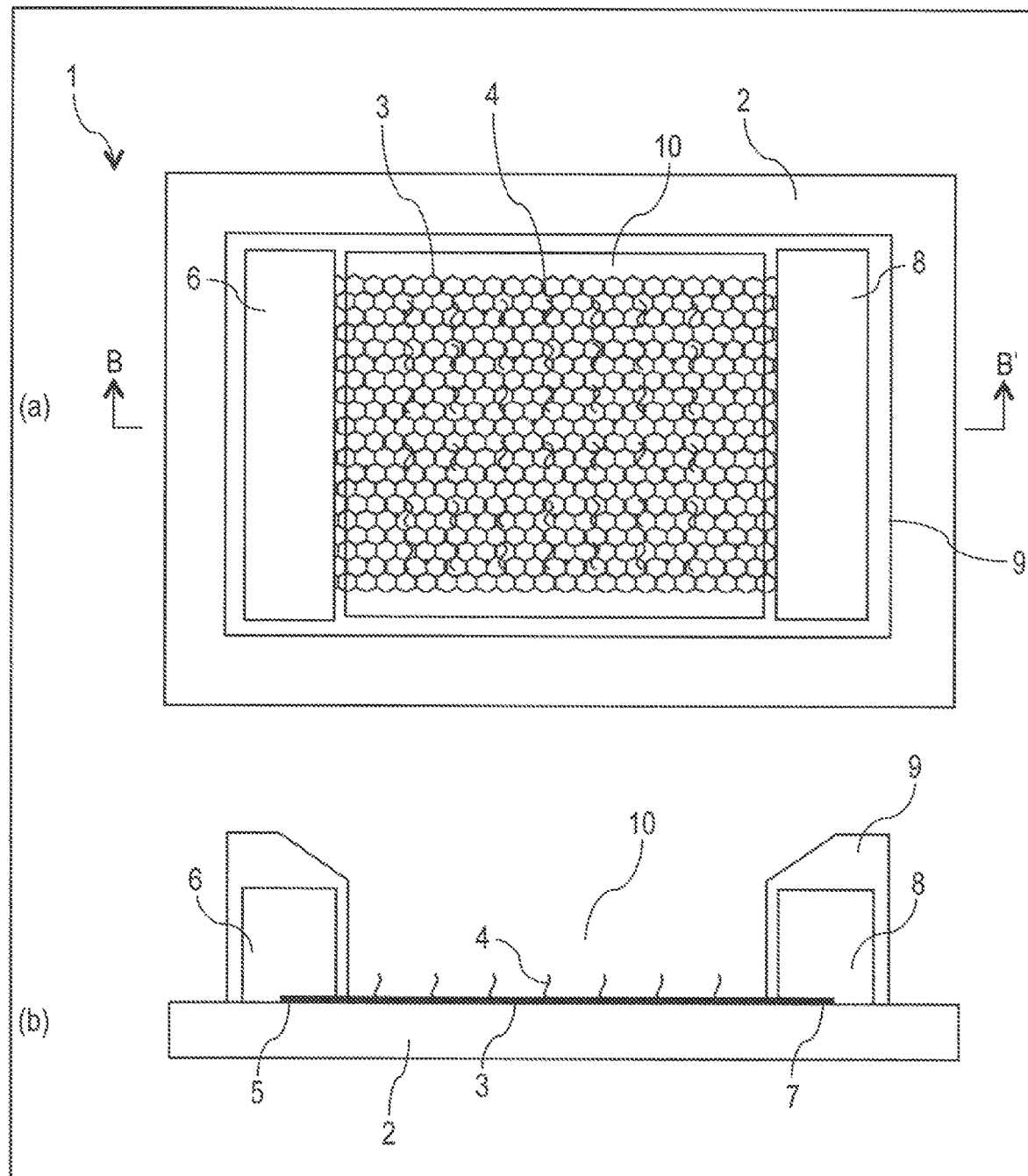
FIG. 1 shows a plan diagram and a sectional diagram of an example of a chemical sensor of an embodiment.

Part (a) of FIG. 1 is a plan diagram showing an example of the chemical sensor of the embodiment. Part (b) of FIG. 1 is a sectional diagram obtained by cutting the chemical sensor 1 of part (a) of FIG. 1 along line B-B'. The chemical sensor 1 includes a substrate 2, at least one surface of which has insulation properties, a channel 3 which is disposed on an insulating surface of the substrate 2, a capturing body 4 which is fixed to a surface of the channel 3 opposite to the substrate 2, a source electrode 6 which is connected to one end 5 of the channel 3, a drain electrode 8 which is connected to the other end 7 of the channel 3, a DC power supply (not shown) which is connected to the source electrode 6 and the drain electrode 8, and a wall portion 9 which is formed of an insulating material.

The wall portion 9 is erected from the surfaces of the substrate 2 and the channel 3 so as to surround a peripheral edge of the exposed channel 3 and to cover outer peripheral surfaces of the source electrode 6 and the drain electrode 8. By the wall portion 9, a sample accommodation portion 10 having the channel 3 as a bottom portion is formed.

Hereinafter, one unit including the substrate 2, the channel 3, the capturing body 4, the source electrode 6, and the drain electrode 8 is also referred to as a "chemical sensor element".

Hereinafter, each configuration will be described.

The substrate 2 has, for example, a rectangular plate shape. For example, the substrate 2 has an insulator on a surface on the channel 3 side. For example, the insulator is formed of silicon oxide, silicon nitride, aluminum oxide, a polymer material, a self-organized film of organic molecules, or the like. For example, other layers are formed of silicon, glass, ceramics, a polymer material, a metal, or the like.

Although described in detail later, the substrate 2 may include an insulator film disposed on the channel 3 side and a conductor layer which functions as a gate electrode. In this case, it is preferable that a thickness of the insulator is as thin as possible within a range which does not impair insulation properties, and for example, it is preferable to set the thickness to approximately several nanometers. For example, such a thin film having high quality can be formed by an Atomic Layer Deposition (ALD) method.

A size of the substrate 2 is, for example, but not limited to, 0.5 to 10 mm×0.5 to 10 mm×0.05 to 1 mm (width×length×thickness).

The channel 3 is disposed on the insulating surface of the substrate 2. The channel 3 is a hexagonal crystal lattice composed of carbon atoms by $sp^2$ binding. In the example of FIG. 1, the channel 3 is a monolayer graphene membrane with a thickness corresponding to one carbon atom. A plurality of layers of graphene films also can be used.

A size of the channel 3 can be, for example, but not limited to, 0.1 to 500 μm×0.1 to 500 μm (width×length). Practically, if the size of the channel 3 is 10 to 100 μm×10 to 100 μm, the channel is easily manufactured.

The capturing body 4 is fixed to the surface of the channel 3 opposite to the substrate 2. The capturing body 4 is a substance which has a specific binding ability to the target substance. For example, the capturing body 4 is an antibody or an antigen binding fragment (for example, Fab, $F(ab')_2$, F(ab'), Fv, scFv, or the like) including a paratope portion, a nucleic acid (DNA, RNA, or the like), an artificial nucleic acid (LNA or the like), an aptamer, a peptide chain (peptide aptamer or the like), lectin, PI polyamide, a receptor protein or a fragment thereof, a compound which binds to a specific substance (phenylboronic acid etc.), a compound which encapsulates a specific substance (cyclodextrin etc.), or the like.

As will be described in detail later, it is preferable that a length of the capturing body 4 is shorter than a Foerster distance between the fluorescent dye binding to the competing substance described later and the channel 3. For example, it is preferable that the capturing body 4 is a molecule having a relatively short length such as the aptamer, the peptide chain, or the antigen binding fragment.

A type of capturing body 4 is selected depending on a type of target substance. For example, in a case where the target substance is the nucleic acid, it is preferable that the capturing body 4 is a single-stranded nucleic acid containing a sequence complementary to a base sequence of the nucleic acid, PI polyamide which recognizes a base pair sequence of a double-stranded DNA and binds to a minor groove, or the like.

In a case where the target substance is the protein or the compound, it is preferable that the capturing body 4 is the aptamer, the peptide chain, the antigen binding fragment, the receptor protein or fragment thereof, or the like.

In a case where the target substance is a sugar chain, it is preferable that the capturing body 4 is the lectin, a phenylboronic acid, or the like.

In a case where the target substance is an antigen, the capturing body 4 may be an antibody or an antigen binding fragment corresponding to the antigen.

In a case where the target substance is a ligand molecule, the capturing body 4 may be a receptor protein or a fragment thereof which binds to the ligand molecule.

In a case where the target substance is a virus or an extracellular vesicle, the capturing body 4 may be an antibody or a fragment thereof which binds to a surface marker of the virus or the extracellular vesicle.

In a case where the target substance is a hydrophobic low molecular weight compound, the capturing body 4 may be any of α-cyclodextrin, β-cyclodextrin, γ-cyclodextrin, or a derivative thereof having an inner diameter capable of encapsulating the target substance.

Figure 2:
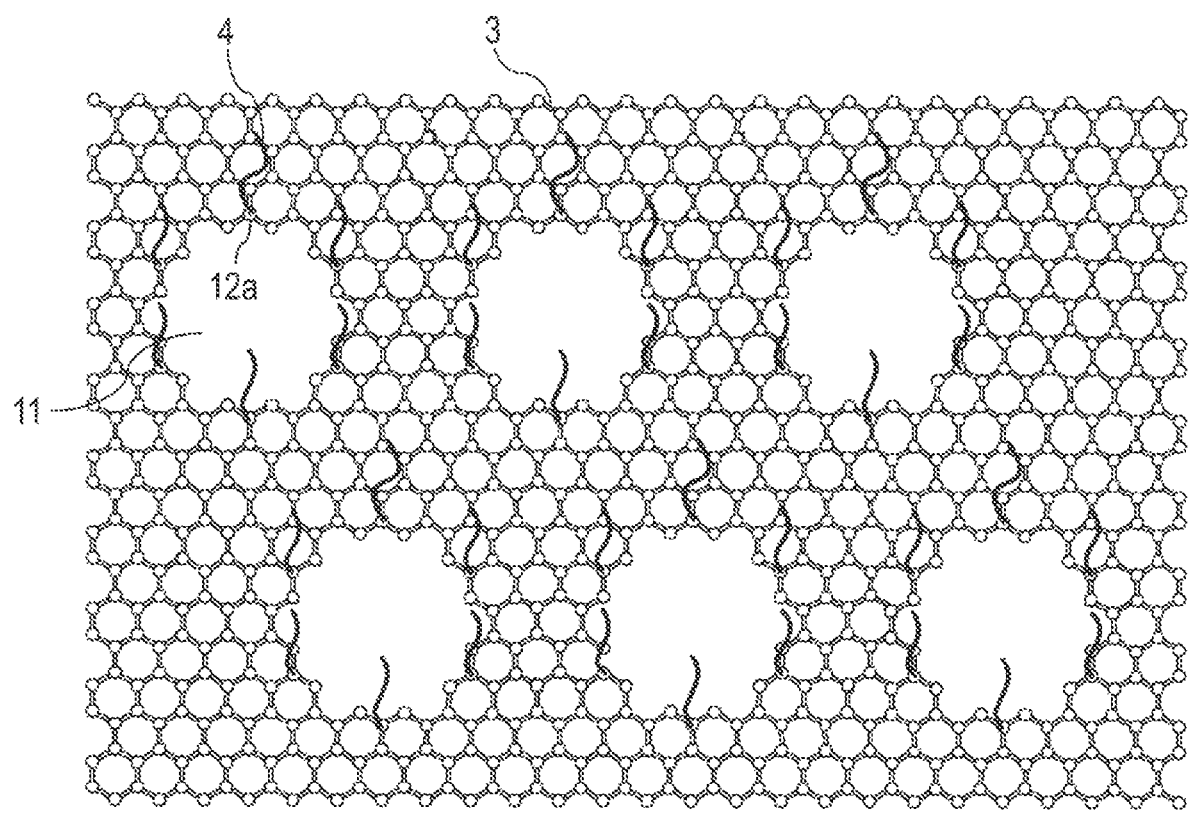
FIG. 2 shows a schematic diagram of an example of a channel of the embodiment.

A method of fixing the capturing body 4 to the channel 3 will be described with reference to FIGS. 2 to 4. FIGS. 2 and 4 are enlarged schematic diagrams of the channel 3 which is the graphene film. White circles indicate carbon atoms. A line between carbon atoms indicates a conjugated double binding between carbon atoms.

As shown in FIG. 2, the graphene film (channel 3) may include an opening 11. For example, a diameter of the opening 11 is 10 nm or less, preferably, 3 nm or less.

In a case where the above graphene film is used, for example, the capturing body 4 can be fixed to a carbon atom 12a existing on an edge of the opening 11 via a chemical binding. For example, the fixing can be performed by substituting a hydrogen atom binding to carbon atom 12a with a functional group, chemically modifying the terminals of the functional group and the capturing body 4 as necessary, and binding the functional group and the capturing body 4 to each other.

The chemical modification is a substitution by a substituent such as, but not limited to, a hydroxy group, a carboxy group, a mercapto group, an amino group, an aldehyde group, a maleimide group, alkyne, an azide group, a histidine group, a Ni-NTA, biotin or the like.

Figure 3:
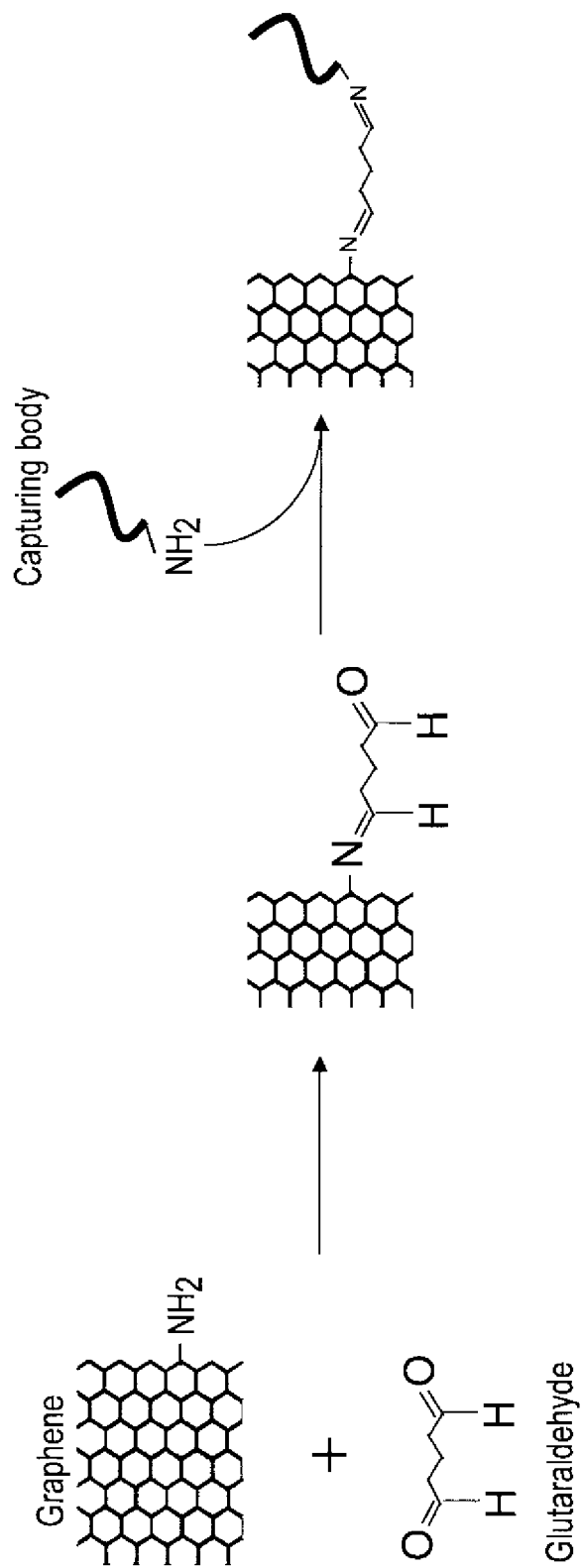
FIG. 3 shows a formula of an example of a method of binding a capturing body to the channel of the embodiment.
Figure 4:
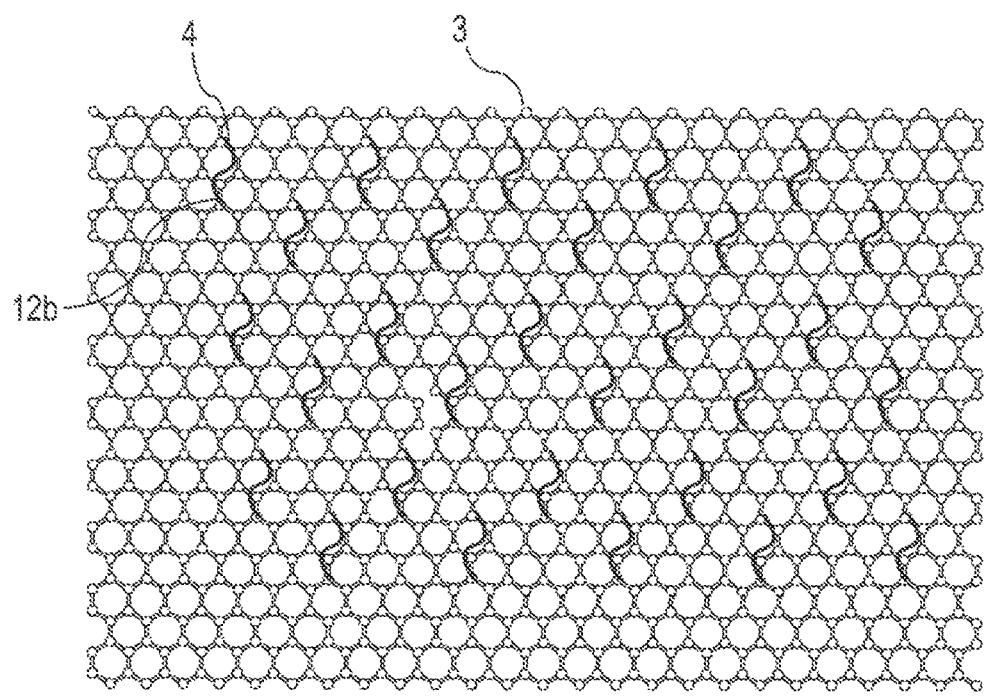
FIG. 4 shows a schematic diagram of an example of a channel of an embodiment.

For example, as shown in FIG. 3, a terminal hydrogen atom may be substituted with an $NH_2$ group by an ammonia plasma treatment or the like, and the $NH_2$ group may be iminated with glutaraldehyde. And then, via the group, the carbon atom 12a existing on the edge of the opening 11 is bound to the capturing body 4 modified at the terminal with the $NH_2$ group.

The capturing body 4 may be fixed to the carbon atom of channel 3 existing on any end exposed to a bottom portion of the sample accommodation portion 10, by the above-described method.

Alternatively, as shown in FIG. 4, the capturing body 4 may be fixed to the carbon atom 12b in a middle of the graphene film (the channel 3). In this case, the carbon atom 12b may be oxidized to generate a modifying group, and the capturing body 4 may bind to the modifying group. For example, the modifying group may be a hydroxy group, a carboxyl group, or the like.

Alternatively, the capturing body 4 may bind to a crystal defect site formed in a manufacturing step of the graphene sheet. For example, by performing an ammonia plasma treatment or the like on a graphene having a crystal defect, a crystal defect portion having a small binding energy to the $sp^2$ binding is modified by $-NH_2$. And thus, with the $-NH_2$ group as a starting point, the binding of the capturing body 4 can be performed.

Alternatively, for example, the terminal of the capturing body 4 may be modified with a pyrenyl group and adsorbed onto a graphene surface by an interaction between a $\pi$ electron of the pyrenyl group and a $\pi$ electron of the graphene.

It is preferable that a plurality of capturing bodies 4 is fixed to the channel 3. And it is preferable that the number of the capturing bodies is as large as possible. For example, it is preferable that the capturing bodies 4 are uniformly dispersed and fixed to the entire surface of the channel 3. The high density and uniform fixing of the capturing body 4 can be realized by any of the above-described methods. According to the method using the opening 11, a density and distribution of the capturing bodies 4 can be controlled using a semiconductor lithography technique.

Also, in cases of the method in which the hydrogen atoms of an end of the opening 11 are substituted, the method in which the crystal defects of the graphene sheet are selectively chemically modified, and the method in which the capturing bodies 4 are adsorbed by using the pyrenyl group, the capturing body 4 can be fixed without destroying the conjugated double binding of the graphene. Therefore, these methods have the advantage that electric characteristics of the graphene, particularly, carrier mobility is not impaired.

The source electrode 6 is disposed on the substrate 2 so as to connect to one end 5 of the channel 3. The drain electrode 8 is disposed on the substrate 2 so as to be connected to the other end 7 of the channel 3. For example, materials of the source electrode 6 and the drain electrode 8 are conductive metals such as gold (Au), silver (Ag), copper (Cu), palladium (Pd), platinum (Pt), nickel (Ni), titanium (Ti), chromium (Cr), or aluminum (Al), or zinc oxide (ZnO), indium tin oxide (ITO), indium gallium zinc oxide (IGZO), a conductive polymer or the like.

For example, as an insulating material of the wall portion 9, a polymer material such as an acrylic resin, polyimide, polybenzoxazole, an epoxy resin, a phenol resin, polydimethylsiloxane, or a fluororesin, an inorganic insulating film such as silicon oxide, silicon nitride, aluminum oxide, or a self-organized film of organic molecules, or the like can be used.

The sample accommodation portion 10 is a container for accommodating the sample to be analyzed and is configured in a liquid-tight manner.

A surface of the channel 3 to which the capturing body 4 is fixed may be covered with a blocking agent. It is preferable that the blocking agent has a hydrophilic portion and the hydrophilic portion is disposed toward the side opposite to the channel 3.

For example, the blocking agent may be phospholipid, polyethylene glycol (PEG) or the like. For example, as a method of covering the surface of the channel 3 with PEG, a method may be used, in which a polycyclic aromatic group such as a pyrenyl group is bound to a terminal of PEG and the surface of the channel 3 and PEG are bound to each other by an interaction between a $\pi$ binding of the polycyclic aromatic group and a $\pi$ binding of the graphene.

By providing the blocking agent, it is possible to prevent hydrophobic impurities from binding to the surface of the channel 3 indicating hydrophobicity. Alternatively, the blocking agent may be a substance which prevents a competing substance described later from nonspecifically binding to the channel 3.

Figure 5:
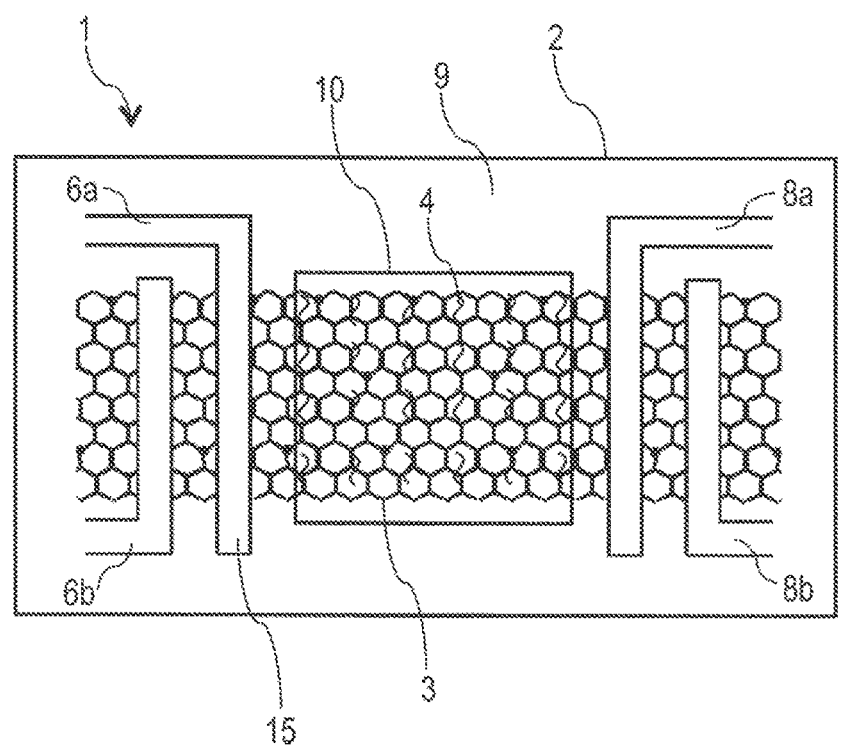
FIG. 5 shows a plan diagram of an example of a chemical sensor of an embodiment.

In another embodiment, two source electrodes and two drain electrodes may be disposed. This example is shown in FIG. 5. The chemical sensor 1 includes a first source electrode 6a, a second source electrode 6b, a first drain electrode 8a, and a second drain electrode 8b. A terminal 15 protruding from each electrode is connected to the channel 3. According to this chemical sensor 1, since a detection can be performed using a four-terminal method, it is possible to more accurately detect a current between the source electrode and the drain electrode (hereinafter, referred to as a "source-drain current"). That is, a large current can be applied between the second source electrode 6b and the second drain electrode 8b, and a potential difference between the first source electrode 6a and the first drain electrode 8a can be measured.

Figure 6:
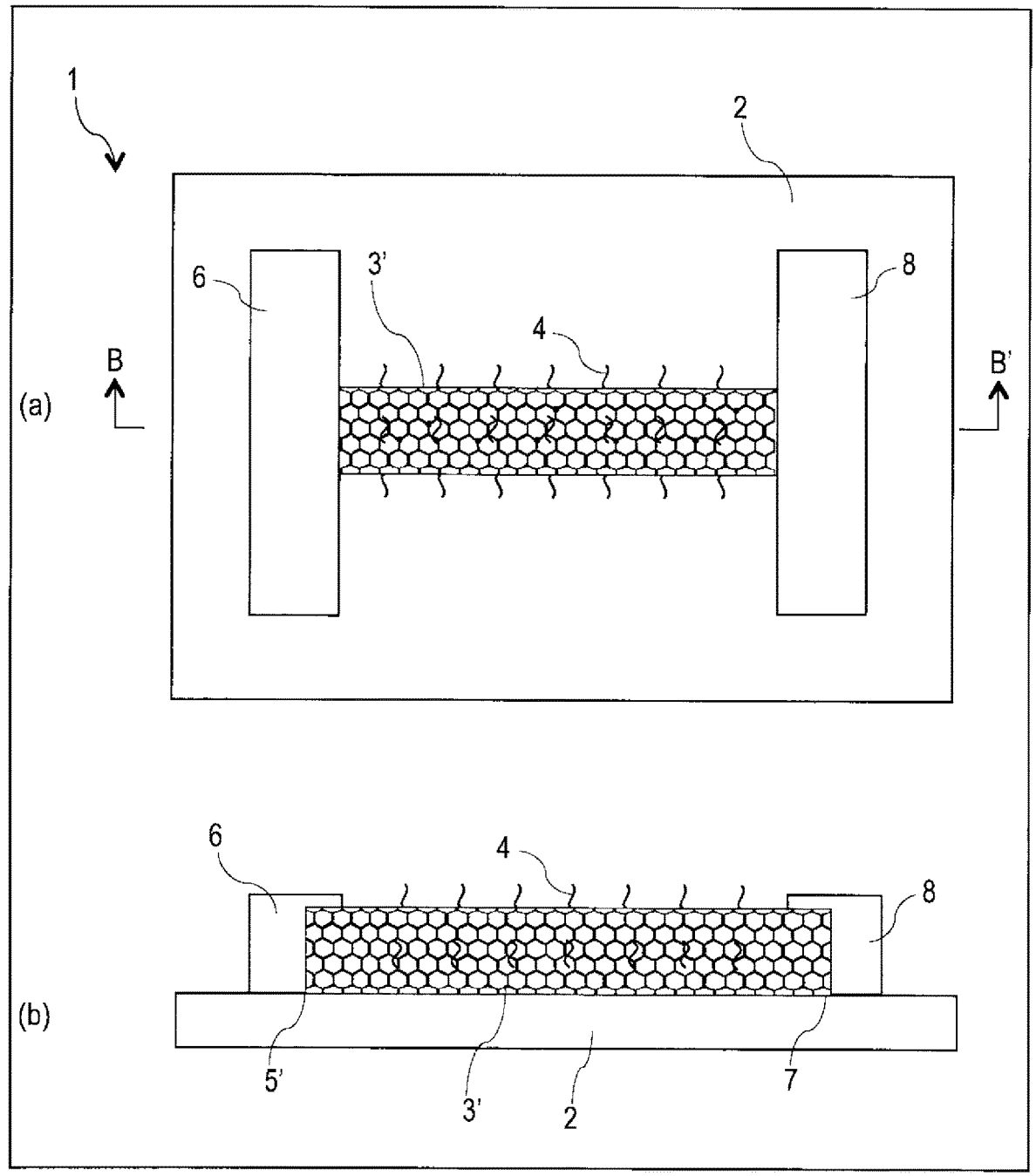
FIG. 6 shows a plan diagram and a sectional diagram of an example of a chemical sensor of an embodiment.

In still another embodiment, the channel 3 may be a carbon nanotube. This example is shown in FIG. 6. In FIG. 6, the wall portion 9 is omitted. A channel 3' of the carbon nanotube has a cylindrical shape. The channel 3' may be a monolayer or multilayers. One end 5' in a longitudinal direction of the channel 3' is connected to the source electrode 6 and the other end 7' is connected to the drain electrode 8.

For example, in a case where the carbon nanotube is used, the capturing body 4 is fixed to an outer-side surface of the channel 3'. For example, for the fixing of the capturing body 4, the method described in FIGS. 2 to 4 can be used. The outer-side surface of the channel 3' may be covered with the above-described blocking agent.

A method of manufacturing the chemical sensor 1 will be described.

A formation of the substrate 2 can be manufactured by any known method in a semiconductor process or the like.

For example, the channel 3 can be formed directly on the substrate 2 using a transfer method from graphite, a chemical vapor deposition (CVD) method, a bottom up growth method, or the like. Or the channel 3 can be temporarily formed on another substrate by a similar method and thereafter it may be transferred to the substrate 2.

The channel 3 having the opening 11 can be formed by photolithography. For example, after an outer periphery of the channel 3 and the opening 11 are selectively exposed by a photoresist, the graphene of the exposed portion is removed by oxygen plasma. Thereafter, if necessary, by performing a hydrogen plasma treatment, the patterned graphene end portion is trimmed into a shape such that a hexagonal crystal lattice is exposed zigzag as shown in FIG. 2. Since this trimming processing is performed in a self-aligning manner, the shape of the patterning of the opening 11 by the photoresist and the oxygen plasma may be circular, for example.

Here, it is difficult to control an angle of a crystal orientation of the channel 3 formed on the substrate 2, and the hexagonal direction of the opening 11 is determined depending on the crystal orientation of the channel 3 in a case where an inner-side end portion of the opening 11 is controlled to have a zigzag shape. Therefore, it is difficult to control the hexagonal direction of the opening 11 on the substrate 2. However, if the self-aligned trimming by the hydrogen plasma treatment is performed, the hexagonal opening is formed in a proper direction in the crystal orientation. That is, even if a manufacturer does not know the crystal orientation of the channel 3 in advance, it is possible to form the opening 11 which faces an optimum orientation in a self-aligning manner. In addition, in a case where the opening 11 has a size of 10 nm or less, it is difficult to perform microfabrication with the photoresist. However, such opening 11 can be formed by using self-organized lithography using a block copolymer.

The source electrode 6, the drain electrode 8, and the wall portion 9 can be manufactured by any known method in the semiconductor process or the like.

The fixing of the capturing body 4 to the channel 3 can be performed by any one of the methods described in FIGS. 2 to 4, after forming a member other than the capturing body 4 in a desired configuration.

Figure 7:
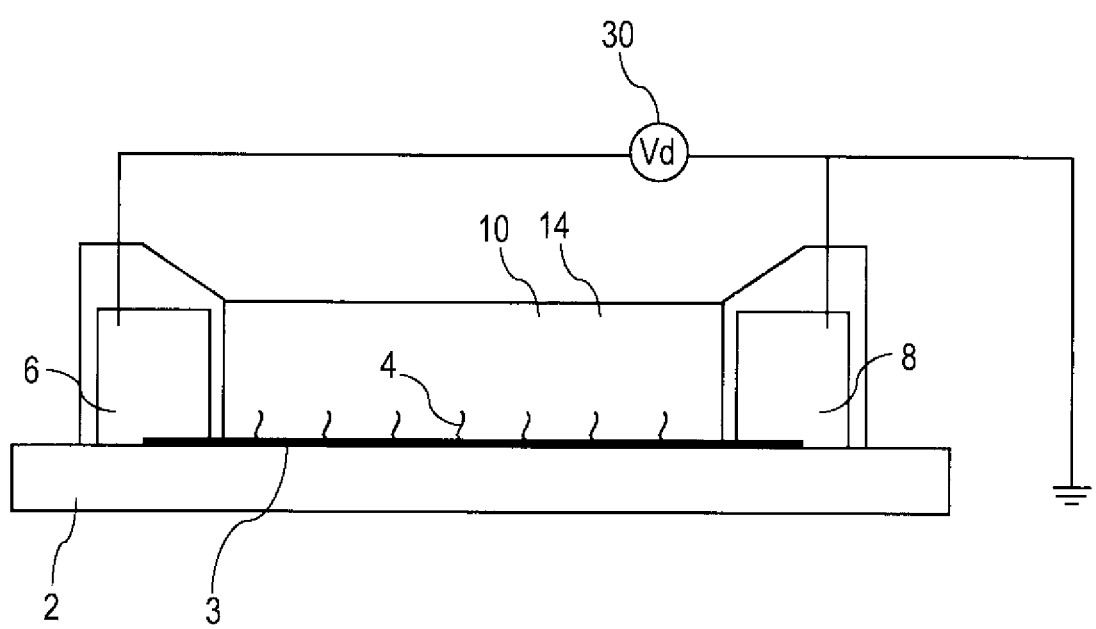
FIG. 7 shows a sectional diagram of an example of the chemical sensor of the embodiment.

FIG. 7 shows a state when the chemical sensor 1 is used. When the chemical sensor 1 is used, a portion above the channel 3, that is, an inside of the sample accommodation portion 10 is filled with a solution 14 such as the reagent containing solution or a mixture solution of the sample and the reagent.

In this example, the source electrode 6 and the drain electrode 8 are connected to a DC power supply 30, and when a source-drain voltage ($V_{sd}$) is applied from the power supply 30, a source-drain current ($I_{sd}$) flows from the source electrode 6 to the drain electrode 8 via the channel 3. A circuit which connects respective members to each other may be formed in the substrate 2.

In still another embodiment, a plurality of chemical sensor elements can be mounted in one sample accommodation portion 10. Alternatively, a plurality of chemical sensor elements each having a sample accommodation portion 10 may be mounted on one substrate 2.

(2) Reagent

The reagent includes the competing substance which is labeled with the fluorescent dye.

The competing substance has the binding ability to the capturing body 4. Accordingly, the target substance and the competing substance compete with each other against the binding to the capturing body 4. For example, the competing substance is a substance which binds to a site of the capturing body 4 to which the target substance binds. For example, the competing substance has the same three-dimensional structure as the binding site of the target substance to the capturing body 4.

The competing substance may be selected so that affinity of the competing substance is slightly weaker than that of the target substance. Thus, the target substance preponderantly binds to the capturing body 4. In this case, even if the target substance has a trace amount and a low concentration, the target substance can reliably bind to the capturing body 4. And thus, detection sensitivity of the target substance having a trace amount and a low concentration increases.

An example of a combination of the target substance, the competing substance, and the capturing body may be, for example, following combination: a target substance which is a low molecular weight compound having a molecular weight of 1000 Da or less, a capturing body which is an antigen binding fragment of an antibody to the target substance, and a competing substance which bind to a paratope portion of the antigen binding fragment; or a neutral target substance having no charge, a capturing body which is an aptamer having a binding ability to the target substance, and a competing substance having a binding ability to the aptamer.

An amount of the competing substance contained in the reagent is selected according to an amount, type or state of the sample to be analyzed, in which the target substance can be contained. For example, it is preferable that the amount of the competing substance in the reagent is sufficiently larger than an amount of the capturing body which can bind to the competing substance. In addition, it is preferable that the concentration is sufficiently high to a dissociation constant of the capturing body and the competing substance.

The competing substance is labeled with the fluorescent dye. The label means that the fluorescent dye binds to the competing substance. For example, the fluorescent dye is a substance which generates a Fluorescence resonance energy transfer (FRET) between the graphene and the fluorescent dye. For example, the fluorescent dye can be fluorescein, rhodamine, Cy dye, Alexa (registered trademark) Fluor, or the like.

Although described in detail later, it is preferable that the fluorescent dye is a fluorescent dye which can be used for time-resolved FRET (TR-FRET). For example, it is preferable that the fluorescent dye is a substance having a fluorescence lifetime of 10 nsec or more. For example, the fluorescent dye is a lanthanoid complex such as a europium complex (Eu($\beta$-NTA)$_3$), or a quantum dot.

It is preferable that the fluorescent dye binds to a site which does not affect the binding of the competing substance to the capturing body 4. The method of binding the fluorescent dye to the competing substance can be performed by any known method. For example, as shown in the formula described below, Fluorescein isothiocyanate (FITC) has the terminal of the fluorescent dye, fluorescein, modified with isothiocyanate group (—N=C=S) and reacts with a primary amine to form a thiourea binding.

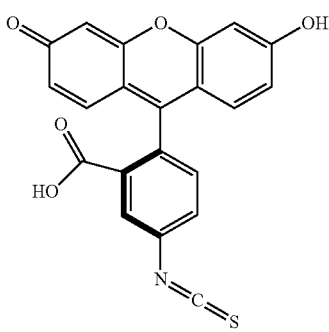

[Formula 1]

Accordingly, if there is a primary amine at a site other than the epitope of the competing substance, or if the site other than the epitope of the competing substance is modified with primary amine, the fluorescent dye can bind at the site.

The reagent may be contained in a solvent. The solvent is, for example, distilled water, sterilized water, physiological saline, a buffer solution, anionic liquid, or the like. For example, the reagent may be contained in a container formed of plastic, glass or the like.

The chemical sensor kit may be provided with a light source for irradiating the channel 3 with excitation light of the fluorescent dye. For example, the light source is an LED light source, a laser light source, or the like. The light source may be, for example, integrally configured with the chemical sensor. In this case, the light source is disposed such that the channel 3 can be irradiated with the excitation light emitted from the light source.

2. Analysis Method

Figure 8:
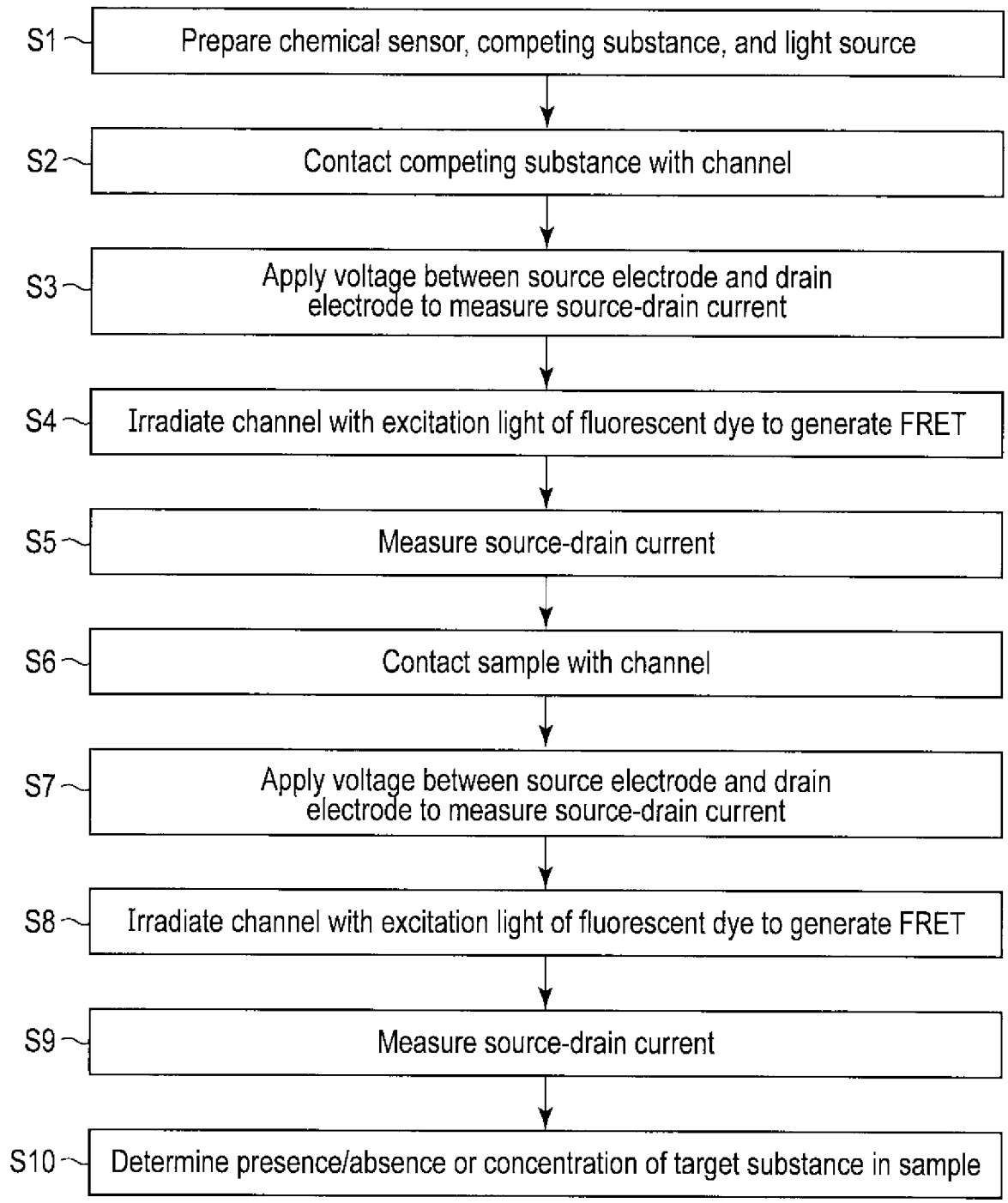
FIG. 8 shows a flowchart of an example of an analysis method of an embodiment.

Hereinafter, an analysis method using the chemical sensor of the embodiment will be described with reference to FIG. 8. FIG. 8 is a schematic flowchart showing an example of an analysis method of a first embodiment.

The analysis method is a method of detecting the target substance in the sample and includes the following steps:

(S1) a step of preparing the chemical sensor of the first embodiment, the competing substance labeled with the fluorescent dye, and the light source for irradiating the channel with the excitation light of the fluorescent dye, (S2) a step of dropping a solution containing the competing substance into a sample accommodation portion to bring the competing substance into contact with the channel, (S3) a step of applying a DC voltage between the source electrode and the drain electrode to measure the source-drain current, (S4) a step of irradiating the channel with the excitation light of the fluorescent dye from the light source to excite the fluorescent dye, thereby transferring the excitation energy of the fluorescent dye labeling the competing substance bound with the capturing body to the channel, (S5) a step of measuring a current between the source electrode and the drain electrode, (S6) a step of dropping a solution containing the target substance into the sample accommodation portion or exposing the sample accommodation portion with a gas containing the target substance to bring the sample into contact with the channel, (S7) a step of applying the DC voltage between the source electrode and the drain electrode to measure the source-drain current, (S8) a step of irradiating the channel with the excitation light of the fluorescent dye from the light source to excite the fluorescent dye thereby transferring the excitation energy of the fluorescent dye labeling the competing substance bound with the capturing body to the channel, (S9) a step of measuring a current between the source electrode and the drain electrode, and (S10) a step of determining presence/absence or an amount of the target substance in the sample based on a result of the measurement.

Hereinafter, a principle of detecting or quantifying the target substance by performing each step will be described.

Figure 9:
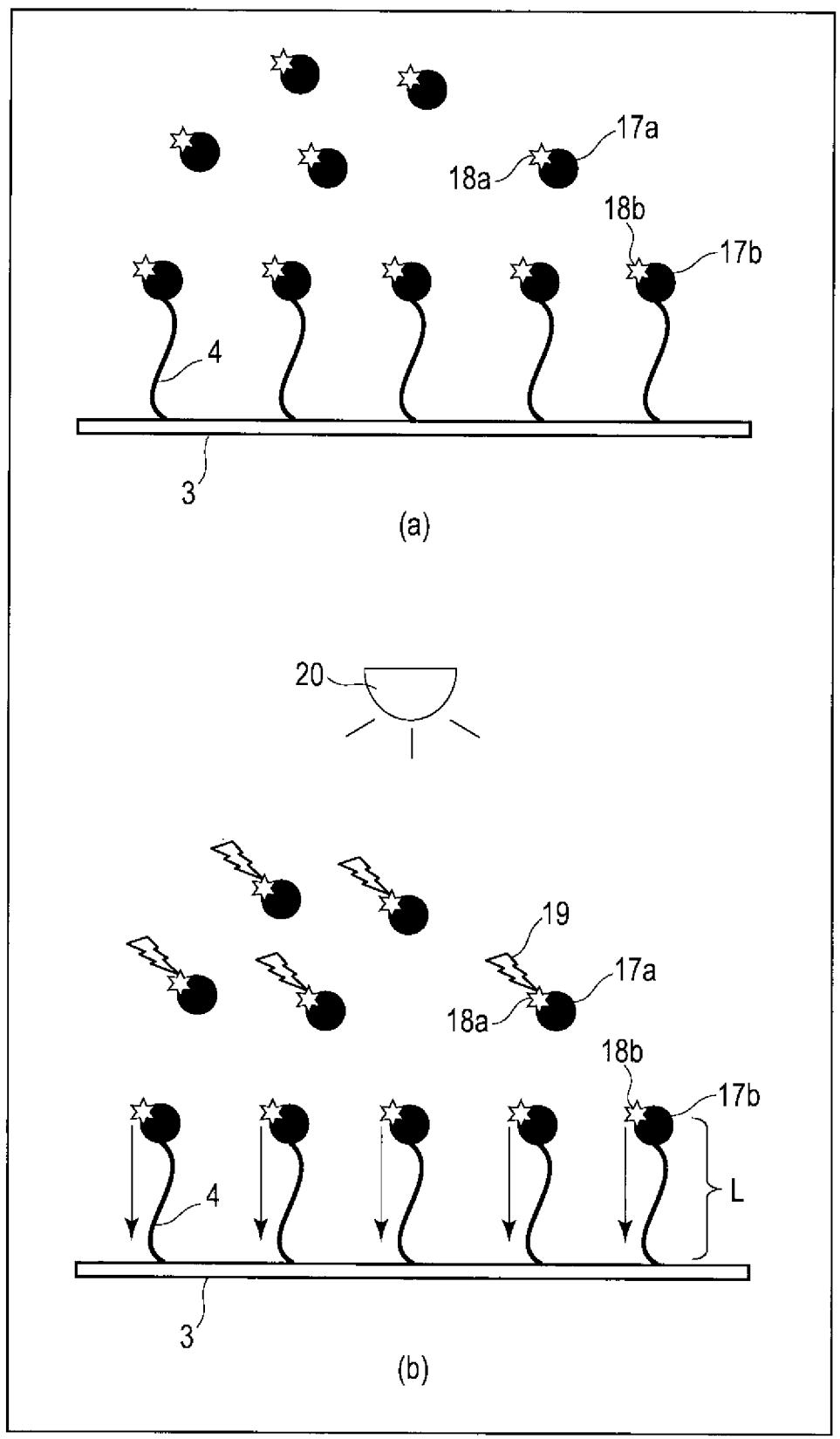
FIG. 9 shows enlarged diagrams of a state when the chemical sensor of the embodiment is used.

First, behaviors of constituent components when the competing substance comes into contact with the channel in the step (S2) will be described with reference to FIG. 9. Part (a) of FIG. 9 is an enlarged diagram of the channel 3. Since the competing substance 17 has a sufficiently large amount compared with an amount of the capturing body 4, the competing substances 17 binds to almost all capturing bodies 4. In FIG. 9, a reference numeral of the competing substance binding to the capturing body 4 is denoted as 17b, and a reference numeral of the fluorescent dye labeling the competing substance 17b is denoted as 18b. In addition, a reference numeral of a surplus competing substance which does not bind to the capturing body 4 is denoted as 17a, and a reference numeral of the fluorescent dye labeling the competing substance 17a is denoted as 18a.

Next, in the step (S3), the voltage is applied between the source electrode and the drain electrode, and the source-drain current is measured in a state where no FRET occurs.

Next, in the step (S4), the channel is irradiated with the excitation light of the fluorescent dye 18 from the light source. Part (b) of FIG. 9 is a schematic diagram showing the competing substances 17a and 17b, the capturing body 4, and the channel 3 in a state the irradiation of the excitation light is applied. By the irradiation of the excitation light the fluorescent dyes 18a and 18b labeling the competing substances 17a and 17b respectively are excited. Since the fluorescent dye 18a labeling the competing substance 17a which does not bind to the capturing body 4 is away from the channel 3, the FRET is not generated between the fluorescent dye 18a and the channel 3. Therefore, the fluorescence 19 is generated. Meanwhile, in the competing substance 17b binding to the capturing body 4, since the fluorescent dye 18b labeling the competing substance 17b is close to channel 3, an energy transfer (FRET, arrows in part (b) of FIG. 9) is generated, where the excitation energy of the fluorescent dye 18b moves to the channel 3. If the FRET is generated, excited electrons from the fluorescent dye 18b are injected into the channel 3 and the fluorescence of the fluorescent dye 18b is quenched or dimmed. In addition, if the electrons are injected into the channel 3 by the FRET, the source-drain current is changed.

For example, the irradiation of the excitation light may be performed at least several picoseconds.

In the step (S5), the source-drain current is measured when the FRET is generated (after the irradiation of the excitation light is applied).

Part (a) of FIG. 10 is a graph showing an example of a relationship of the source-drain current ($I_{sd}$) with respect to a gate voltage ($V_g$). For example, this graph can be obtained by measuring the $I_{sd}$ while changing the $V_g$. A solid line indicates the relationship in a state before the irradiation of the excitation light in which the FRET is not generated (the state in the step (S3)). A broken line indicates the relationship after the FRET is generated by the irradiation of the excitation light (the state of the step (S5)).

Since the graphene has bipolar characteristics, the graphene can be in the state where electrons are carriers or in the state where voids are carriers. Accordingly, the relationship between the $V_g$ and the $I_{sd}$ shows a V shape as shown in part (a) of FIG. 10. That is, in a case where the $V_g$ is applied negatively, with a charge neutral point at which the $I_{sd}$ is the lowest as a center, the $I_{sd}$ rises as a hole (positive hole) serves as the carrier, and in a case where the $V_g$ is applied positively, the $I_{sd}$ rises as the electron serves as the carrier.

Figure 11:
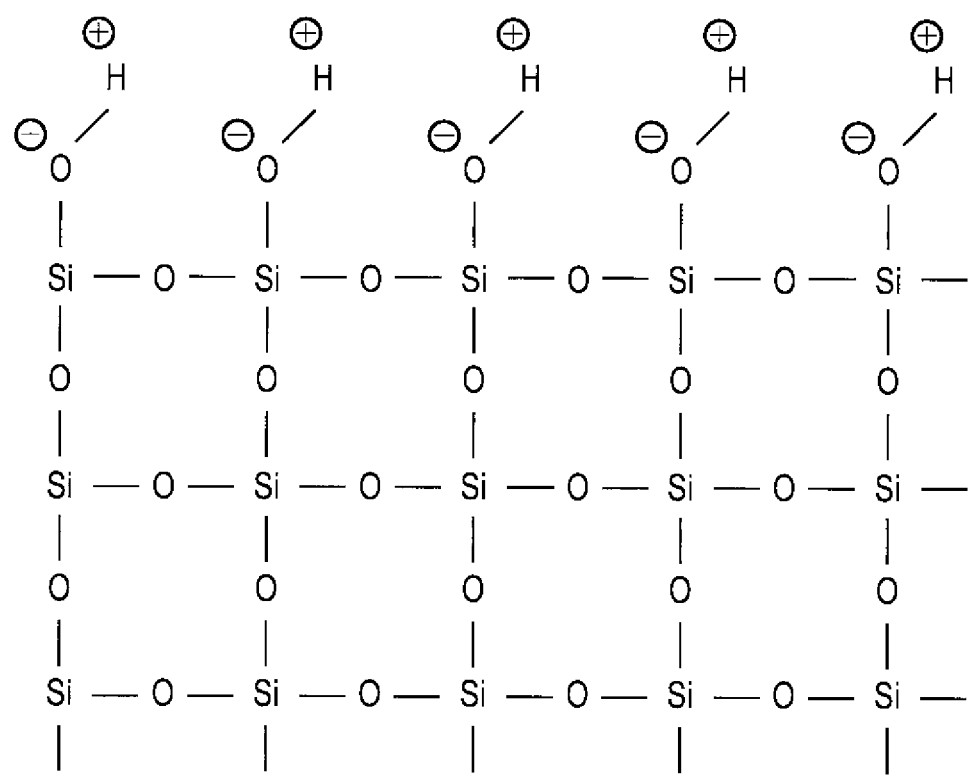
FIG. 11 shows an enlarged diagram of silicon oxide.

In addition, the charges from surrounding materials are injected into the graphene, and thus, in most cases, the charge neutral point of the graphene may be shifted from 0 V. For example, when silicon oxide is used as the graphene base (i.e., the insulator of the substrate 2), as shown in FIG. 11, since the hydrogen atoms positioned at a tip of Si—O—H positioned the terminal of silicon oxide are charged with positive charges, the positive charges are injected into the graphene from here, and the charge neutral point is shifted to a plus side as shown in part (a) of FIG. 10.

If the excited electrons are injected from the fluorescent dye 18b into the channel 3 by the occurrence of the FRET as described above, the charge neutral point is apparently shifted toward a minus side of a $V_g$ axis as shown by the broken line in part (a) of FIG. 10. Alternatively, an inclination of the graph becomes loose as indicated by the broken line in part (b) of FIG. 10. In the case of the chemical sensor of FIG. 1 in which the gate electrode is not used, for example, the source-drain current is detected as the gate voltage=0 V. In the case of the gate voltage=0 V, the source-drain current decreases due to the above-described shift. Therefore, by obtaining a difference between the source-drain current measured in the step (S3) and the source-drain current measured in the step (S5), it is possible to detect a characteristic change corresponding to the energy transfer in the case where the FRET is generated at the positions of all capturing bodies 4.

Next, in the step (S6), the sample including the target substance comes into contact with the channel. For example, in a case where the sample is a liquid, the contact can be performed dropping the sample in the sample accommodation portion. Alternatively, in a case where the target substance is a gaseous component and the sample is a gas, for example, the sample accommodation portion is previously filled with a solution, and then, the sample accommodation portion is exposed by the gas sample, and the sample may come into contact with the channel via dissolution of the target substance in the solution in the sample accommodation portion. FIG. 12 are enlarged schematic diagrams showing a state where the target substance 16 comes into contact with the channel 3 and the binding between the capturing body 4 and the target substance 16 competes with the competing substance 17. In a case where the amount of the target substances 16 is small or the concentrations thereof are low, as shown in part (a) of FIG. 12, a smaller amount of the bindings of the competing substance 17b to the capturing bodies 4 are replaced with the target substances 16, and thus, the target substances 16 bind to the capturing bodies 4 and replaced competing substances 17b are released into the solution 14. When the amount of the target substances 16 is large or concentrations thereof are high, as shown in part (b) of FIG. 12, the binding of the competing substance 17b is replaced with the target substances 16 at many capturing bodies 4, and, many target substances 16 bind to these capturing bodies 4. That is, a ratio of the numbers of target substances 16 and competing substances 17 binding to the capturing bodies 4 is proportional to a ratio of the amounts of existence of the target substances 16 and the competing substances 17 in a mixture accommodated in the sample accommodation portion. Here, since the amount of the competing substances 17 is constant after being supplied in the step (S2), the ratio of the numbers of the target substances 16 and the competing substances 17 binding to the capturing bodies 4 is determined according to the number of target substances 16 or concentrations thereof.

Next, in the step (S7), a voltage is applied between the source electrode and the drain electrode, and the source-drain current is measured in a state where the FRET is not generated (i.e., irradiation of excitation light is not applied). The source-drain current in the state where the FRET is not generated is measured once in the step (S3), but a composition of the solution in the sample accommodation portion coming into contact with the channel 3 is changed from the case of the step (S3), and thus, a measurement is performed so as to correct the change due to the influence.

Figure 13:
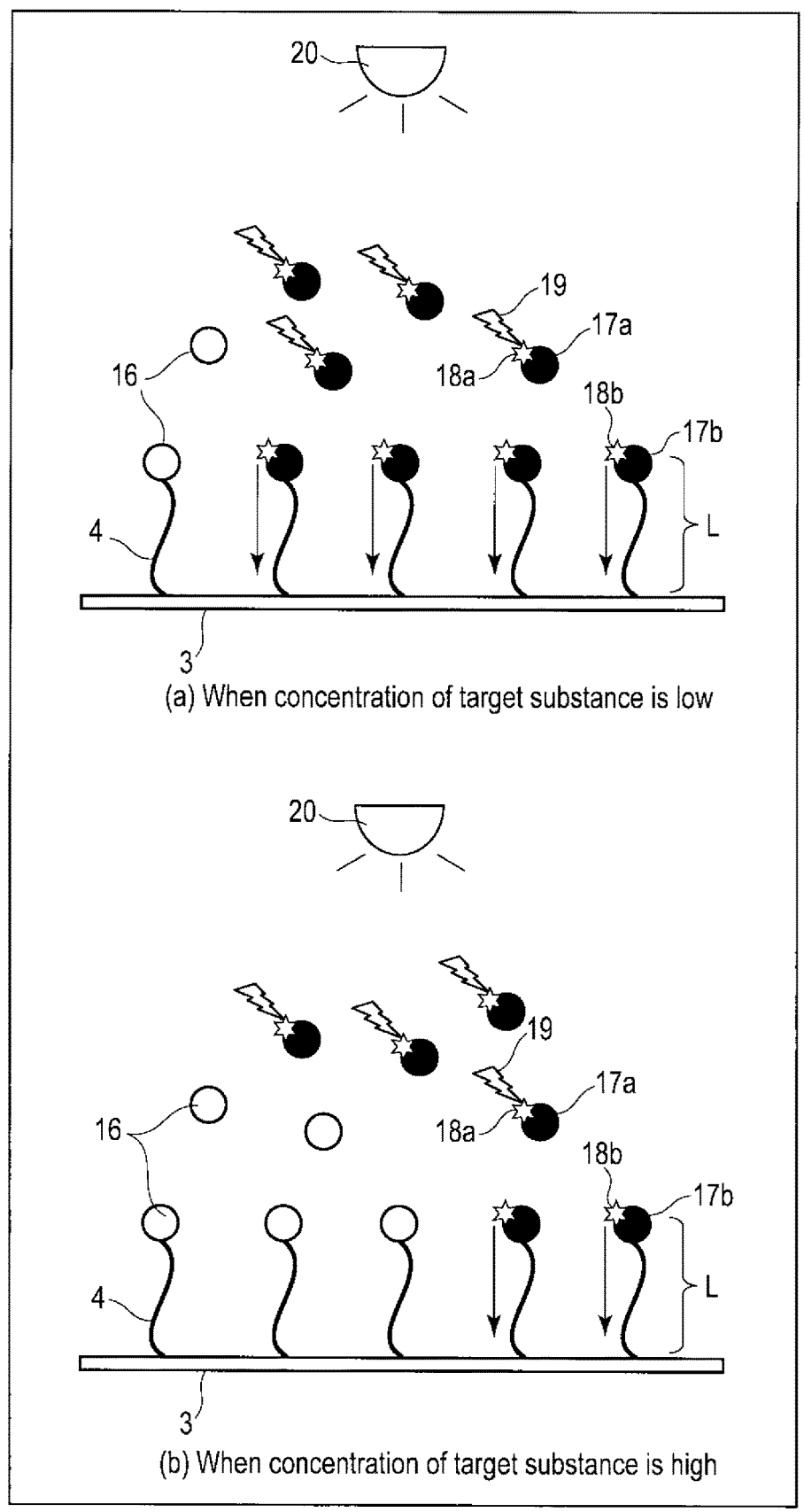
FIG. 13 shows enlarged diagrams of a state when the chemical sensor of the embodiment is used.

Next, in the step (S8), the channel is irradiated with the excitation light of the fluorescent dye 18 from the light source. FIG. 13 are schematic diagrams showing the target substance 16, the competing substance 17, the capturing body 4, and the channel 3 in a state where the irradiation is applied by the excitation light from the light source 20. By the irradiation of the excitation light the fluorescent dyes 18a and 18b which respectively label the competing substances 17a and 17b are excited, and in the competing substance 17b binding to the capturing body 4, the fluorescent dye 18b generates the energy transfer by the FRET with the channel 3. Meanwhile, the target substance 16 is not fluorescently labeled, and thus, the FRET is not generated in a portion where a partner binding to the capturing body 4 is replaced by the target substance 16. Compared to the case where the amount of target substances 16 is small or concentrations thereof are low (part (a) of FIG. 13), when the amount of the target substances 16 is large or concentrations thereof are high (part (b) of FIG. 13), an amount of energy transfer due to the FRET decreases.

Figure 14:
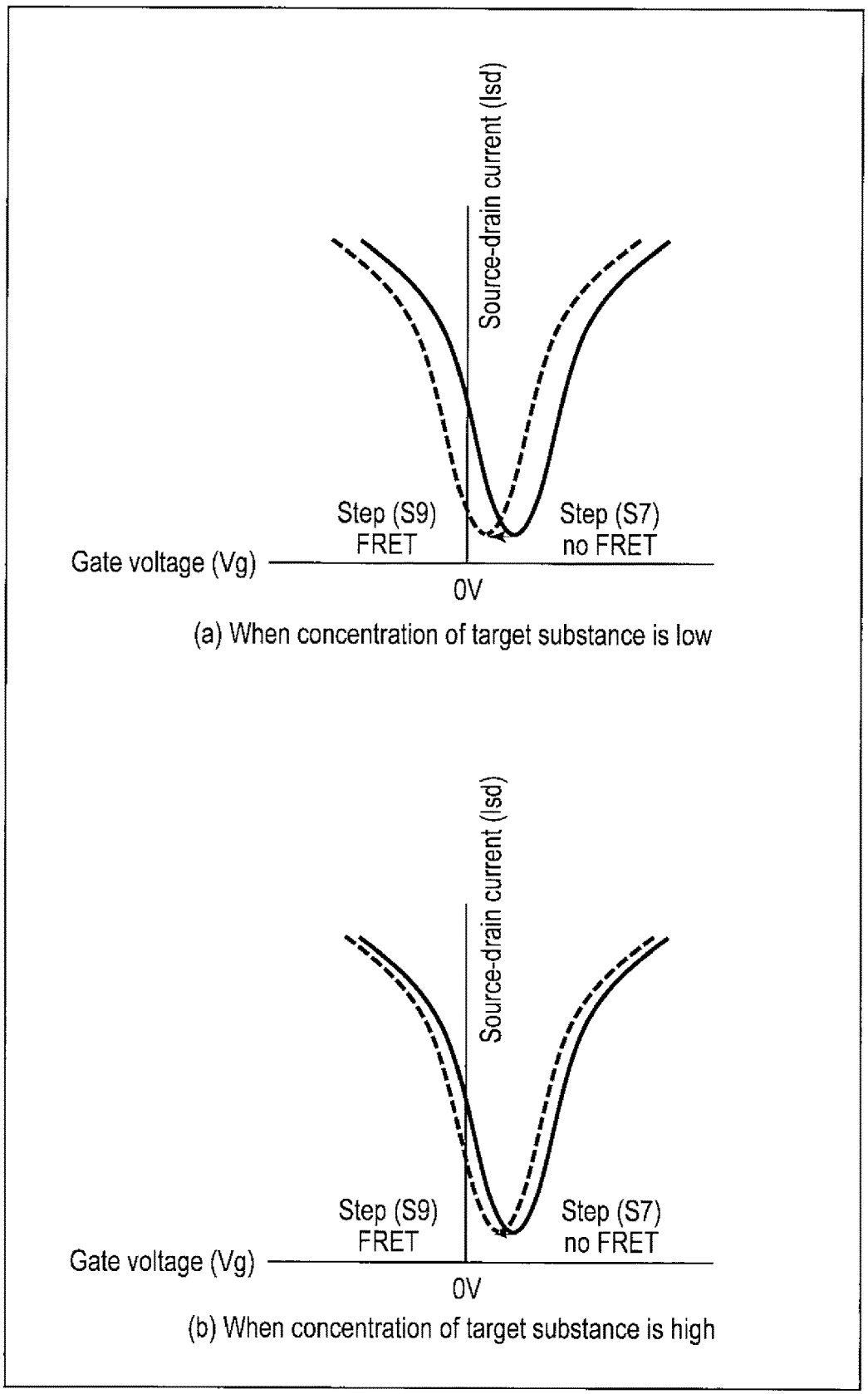
FIG. 14 shows graphs of the relationship between the $V_g$ and the $I_{sd}$.

As described above, a state in which a magnitude of the FRET is changed with respect to the measurement in the step (S7) by competitions of the target substance 4 and the competing substance 17 in binding to the capturing body 4 is measured as source-drain current in the step (S9). FIG. 14 are graphs showing a relationship of the source-drain current ($I_{sd}$) with respect to the gate voltage ($V_g$) in this case. When the amount of the target substances 16 is small or concentrations thereof are low, as shown in part (a) of FIG. 14, $V_g$-$I_{sd}$ characteristics measured in the step (S9) in which the FRET is generated shift larger toward a minus side than $V_g$-$I_{sd}$ characteristics measured in the step (S7) in which the FRET is not generated. Meanwhile, when the amount of the target substances 16 is large or concentrations thereof are high, as shown in part (b) of FIG. 14, the shift of the $V_g$-$I_{sd}$ characteristics of the FRET according to the presence/absence decreases.

Figure 15:
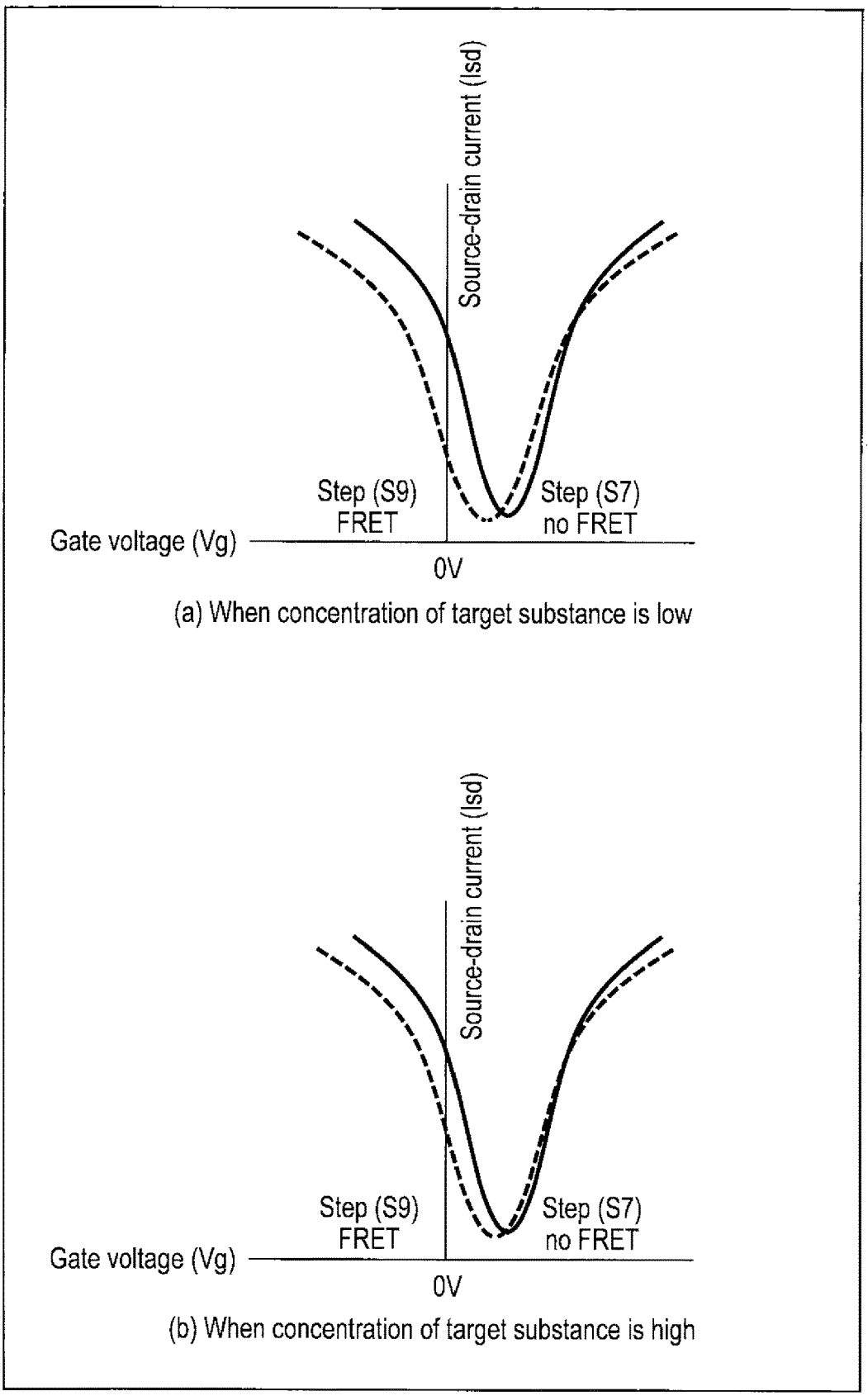
FIG. 15 shows graphs of the relationship between the $V_g$ and the $I_{sd}$.

Alternatively, in the step (S5), if a change in the $V_g$-$I_{sd}$ characteristics shows the behavior that the inclination is also changed as shown in part (b) of FIG. 10, as shown in part (a) of FIG. 15, the amount of change in the inclination is changed according to the amount of the target substances 16. That is, when the amount of the target substances 16 is small or concentrations thereof are low, as shown in part (a) of FIG. 15, the change of the inclination of the $V_g$-$I_{sd}$ characteristics increases. Meanwhile, when the amount of the target substances 16 is large or concentrations thereof are high, as shown in part (b) of FIG. 15, the change of the inclination decreases.

In the case of the chemical sensor of FIG. 1 without the gate electrode, the behavior is calculated as the change of the source-drain current in the gate voltage=0 V.

In the step (S10), the presence/absence or the amount of the target substances is determined based on the result of the measurement.

Figure 16:
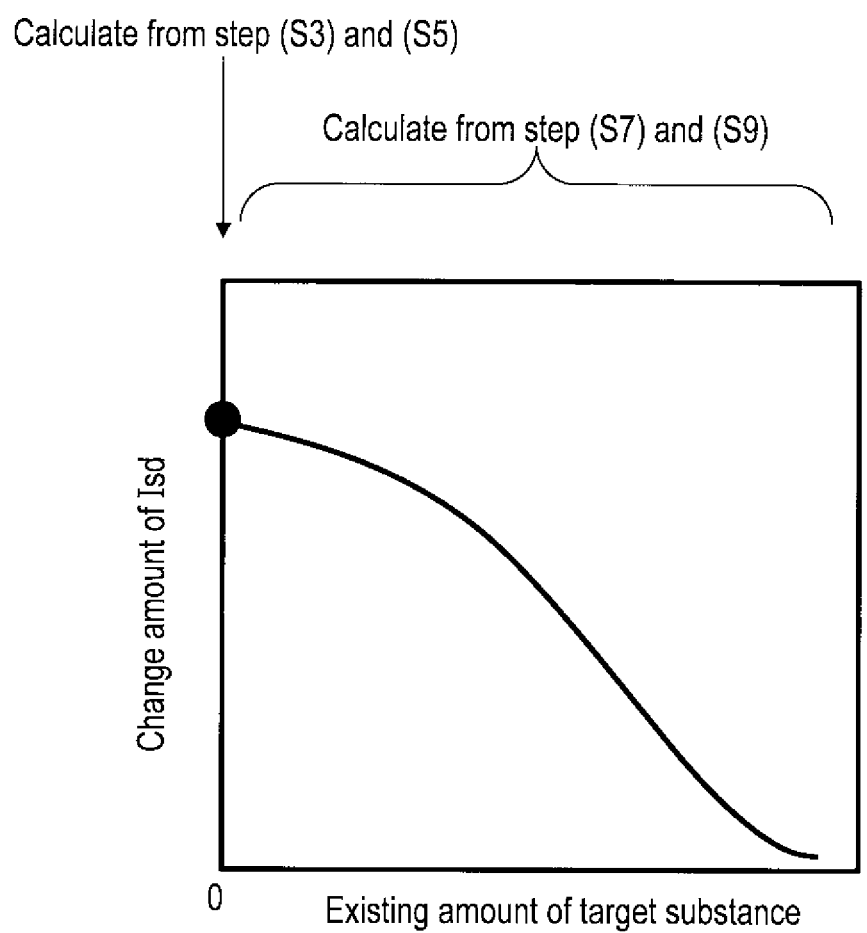
FIG. 16 shows a graph of an example of a relationship between an amount of change of the $I_{sd}$ and an amount of existence of a target substance.

FIG. 16 shows an example of a relationship between the amount of change of the $I_{sd}$ and the amount of existence of the target substance in the sample. As the amount of the target substances increases, the amount of change of the $I_{sd}$ decreases.

Here, the amount of change of the $I_{sd}$ in a case where the target substance does not exist can be determined from the difference (amount of change) between $I_{sd}$'s measured in the step (S3) and the step (S5). In a case where the difference (amount of change) of the $I_{sd}$'s measured in the step (S7) and the step (S9) coincides with the difference between the step (S3) and the step (S5), or in a case where no significant difference is found, it can be determined that "the target substance does not exist in the sample or the target substance exists only equal to or less than a detection limit".

Meanwhile, in a case where the difference between $I_{sd}$'s measured in the step (S7) and the step (S9) is significantly smaller than the difference between $I_{sd}$'s measured in the step (S3) and the step (S5), it can be determined that the "target substance exists in the sample".

Alternatively, the amount of the target substance may be determined from the amount of change of the $I_{sd}$. For example, the determination of the amount of the target substance may be performed using a calibration curve. The determination can be performed by the following steps: preparing the calibration curve of the amount of change of the $I_{sd}$ with respect to the amount of existence of the target substance using a plurality of standard samples in which the amounts of existence of the target substances are known and the amounts of existence are different from each other, and comparing this calibration curve with a measurement result using the sample analyzed. Accordingly, it is possible to calculate the amount of existence of the target substance in the sample.

According to the analysis method described above, the competing substances 17 whose amount corresponds to the amount of existence of the target substances 16 bind to the capturing body 4, and the fluorescent dye 18 in the competing substance 17 binding to the capturing body 4 generates the FRET. As a result, the $I_{sd}$ is changed. Thereby, it is possible to accurately detect or quantify the target substance 16.

Therefore, for example, even in a case where unknown impurities exist in the sample and the impurities bind or are adsorbed to the surface of the channel 3, the FRET is not generated as long as the impurities are not fluorescence substances. And thus, the amount of change of the $I_{sd}$ dependent on the presence/absence of the FRET is not affected. Therefore, the detection result is prevented from being a false negative or a false positive. Thereby, it is possible to accurately detect or quantify the target substance. Moreover, even if the impurities have autofluorescence, the presence of the impurities can be detected by fluorescently observing the fluorescence of the sample in advance, and the result of the observation can be taken into account when performing the step (S10).

Moreover, in the case where there is a possibility that unknown impurities are mixed in the sample, in the related art, it is extremely difficult to select a blocking agent for avoiding influences of the impurities. In addition, it is impossible to perform preliminary verification of impurities because it is unknown, and thus, in principle, reliability lacks. Meanwhile, according to the chemical sensor and the analysis method of the embodiment, it is only necessary to avoid nonspecific adsorption to the channel 3 of the competing substance 17a and the fluorescent dye 18a which does not bind to the capturing body 4, and thus, selection of the blocking agent is easy, and it is possible to verify the effects of the blocking agent in advance.

In addition, the chemical sensor and the analysis method of the embodiment uses, as an index, the amount of change of the $I_{sd}$ between the case where the irradiation of the excitation light is applied (step (S4)) and the case where the irradiation of the excitation light is not applied (step (S6)). Accordingly, even in a case where the composition of the sample or pH thereof fluctuates due to any reason during the analysis, the measurement is performed based on the $I_{sd}$ without the excitation light at that time, and thus, the influences therefrom can be eliminated. Thereby, it is possible to accurately detect or quantify the target substance.

Moreover, since the chemical sensor and the analysis method of the embodiment uses, as an index, the $I_{sd}$ by the FRET using the fluorescently labeled competing substance, it is possible to detect an uncharged substance or a low molecular weight compound which is not easily detected in the method of the related art.

In addition, since the chemical sensor and the analysis method of the embodiment uses the $I_{sd}$ as an index, it is possible to miniaturize an analyzer including the chemical sensor. Moreover, it is possible to perform an electrical analysis without a microscopic observation, and thus, it is possible to detect the target substance regardless of a location of the analysis. For example, it is possible to perform the detection in a facility, a household, on the outside, or the like which is not equipped with a microscope.

The above-described steps (S3) to (S5) may be performed or may not be performed as necessary. For example, as described above, by comparing the measurement result of the step (S5) with the measurement result of the step (S9), it is possible to more accurately perform the analysis, particularly in a case where there is no target substance. In addition, in a case where the analysis is repeated plural times under the same condition, these steps of the second and subsequent times can be omitted and the results measured in (S8) in the previous analysis can be used. Alternatively, the result of the step (S7) may be estimated from previously obtained findings and the step (S10) may be performed using the estimated result.

It is preferable to select the size of the capturing body 4 used in the analysis method in consideration of the following. A rate (FRET efficiency) at which the energy of the fluorescent dye 18b is moved by the FRET is expressed by the following formula (I) known as Foerster's expression and is approximately inversely proportional to the sixth power of the distance between the fluorescent dye 18b and the channel 3:

$$E = 1/(1+(r/R_0)^6) \quad (I)$$

E: FRET efficiency
r: distance between donor and acceptor $R_0$: Foerster distance (E=distance between donor and acceptor when E=50%)

Therefore, it is preferable that a distance L from the portion of the channel 3 where the capturing body 4 is fixed to the site of the capturing body 4 to which the target substance 16 or the competing substance 17b binds is shorter than the Foerster distance. Accordingly, it is preferable that the size of the capturing body 4 is also selected in consideration of this. For example, the Foerster distance is 3 to 10 nm, and in the case of a fluorescence protein, the Foerster distance is approximately 5 nm.

The sample used in the analysis method is an analysis subject which can contain the target substance. For example, the sample is a liquid. Alternatively, the sample is a gas. For example, the sample may be a biological material, a material derived from an environment, a material derived from food or beverage, a material derived from an industrial source, an artificially prepared preparation, any combination thereof, an odor component or other volatile component generated from these, or the like.

Alternatively, the sample may be a preparation prepared from the above-described materials. For example, the preparation may be prepared by any of well-known pretreatments such as mincing, homogenizing, dissolving, suspending, diluting, concentrating, purifying, vaporizing, or extracting, in order to use any of the above-described materials as the sample according to the present embodiment.

For example, the biological sample is a sample derived from an animal, a plant or a microorganism. For example, a biological sample is biological substances such as blood, serum, plasma, blood cell, urine, stool, sweat, saliva, buccal mucosa, sputum, lymph, cerebrospinal fluid, tears, breast milk, amniotic fluid, semen, tissue, biopsy, cultured cells, plant cells, plant extracts, or exhaled breath, mixtures thereof, or the like.

A sample, which is an environment-derived material, is soil, river water, seawater, air, a mixture thereof, or the like.

For example, the target substance is a substance which serves as an index of a property, a state and/or a change of the organism, material or environment from which the sample is derived. In a case where the sample is the biological sample, the property and the state are, for example, health conditions of organisms from which the sample is derived. For example, the health condition is presence or absence, characteristics, severity, a course of a disease, and/or an effect or a side effect on a medicinal product in the organism. Alternatively, the health condition is virus or microorganism which infects the organism and is contained in the sample.

For example, the target substance is a nucleic acid, a protein, an endocrine cell, a cell, a blood cell, a virus, a microorganism, an organic compound, an inorganic compound, or a low molecular weight compound, such as an odor component, a volatile organic chemical substance, or the like.

In the above-described analysis method, the contacts of the competing substance and the sample with respect to the channel 3 in the step (S2) and the step (S6) respectively are performed by accommodating the competing substance and the sample in the sample accommodation portion 10 respectively, for example. For example, the accommodation may be performed by dropping with a pipette, an ink jet, a dispenser, or the like. Alternatively, for example, the contact of the sample with respect to the channel 3 in the step (S2) may be performed by exposing a liquid on the sample accommodation portion to a gas containing the sample. For example, the gas containing the sample may be blown, or the chemical sensor of the embodiment may be disposed in a gas atmosphere containing the sample.

In the analysis method, for example, the steps (S2) to (S10) may be performed by a device which automatically performs each step. For example, the device includes a lighting unit including a light source, a power supply for applying a DC voltage to a chemical sensor and between a source electrode and the drain electrode, a measurement unit that detects the $I_{sd}$, and a control unit. The control unit is electrically connected to the lighting unit and the measurement unit, controls the behavior of each unit, and determines the presence/absence or the amount of the target substance from the detection result in the measurement unit. The step (S10) may be automatically performed by a computer having a program.

In still another embodiment, the analysis method may be performed using a time-resolved FRET (TR-FRET). By using the TR-FRET, it is possible to efficiently remove the FRET by impurities having the autofluorescence of a normal fluorescence lifetime. Hereinafter, an analysis method using the TR-FRET will be described.

In a case where the TR-FRET is used, a substance having the fluorescence lifetime of 10 nsec or more is used as the fluorescent dye. For example, as the fluorescent dye, it is preferable to use the lanthanoid complex such as a europium complex or a quantum dot. For example, the fluorescence lifetime of the europium complex is approximately 500 msec, and the fluorescence lifetime of the quantum dot is approximately 20 nsec. Meanwhile, a general organic fluorescent dye has a fluorescence lifetime of approximately several nanoseconds, and for example, the fluorescence lifetime of the above-described FITC is approximately 4.5 ns.

FIG. 17 shows relationships between intensities and times of a fluorescent dye having the fluorescence lifetime of 10 nsec or more (hereinafter, also referred to as a "fluorescent dye having a long fluorescence lifetime") and a fluorescent dye of ordinary organic molecules. If the irradiation of the excitation light is performed, the fluorescence is generated in both. However, after the irradiation of the excitation light is stopped, the fluorescence from the ordinary fluorescent dye is quenched by approximately several nanoseconds. Meanwhile, the fluorescent dye having a long fluorescence lifetime can generate the fluorescence even after 10 nsec.

Figure 18:
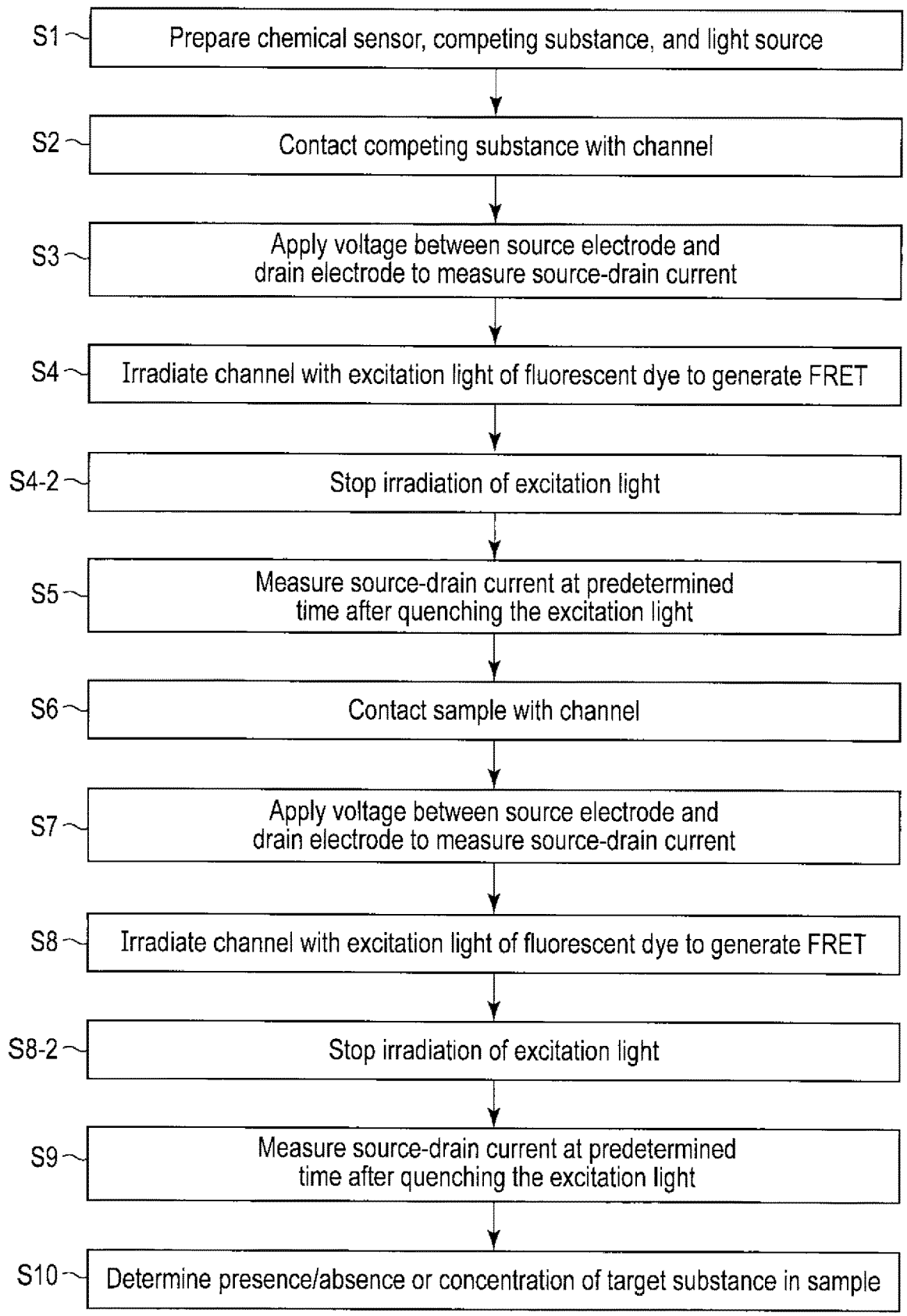
FIG. 18 shows a flowchart of an example of an analysis method of an embodiment.

The analysis method using the TR-FRET includes the following steps shown in FIG. 18:

(S1) a step of preparing the chemical sensor of the first embodiment, the competing substance labeled with the fluorescent dye, and the light source for irradiating the channel with the excitation light of the fluorescent dye, (S2) a step of dropping a solution containing the competing substance into a sample accommodation portion to bring the competing substance into contact with the channel, (S3) a step of applying a DC voltage between the source electrode and the drain electrode to measure the source-drain current, (S4) a step of irradiating the channel with the excitation light of the fluorescent dye from the light source to excite the fluorescent dye thereby transferring the excitation energy of the fluorescent dye labeling the competing substance bound with the capturing body to the channel, (S4-2) a step of stopping the irradiation of the excitation light, (S5) a step of measuring the current between the source electrode and the drain electrode after a predetermined time elapses after the step (S4-2) is performed, (S6) a step of dropping a solution containing the target substance into the sample accommodation portion or exposing the sample accommodation portion with a gas containing the target substance to bring the sample into contact with the channel, (S7) a step of applying the DC voltage between the source electrode and the drain electrode to measure the source-drain current, (S8) a step of irradiating the channel with the excitation light of the fluorescent dye from the light source to excite the fluorescent dye thereby transferring the excitation energy of the fluorescent dye labeling the competing substance bound with the capturing body to the channel, (S8-2) a step of stopping the irradiation of the excitation light, (S9) a step of measuring the current between the source electrode and the drain electrode after a predetermined time elapses after the step (S8-2) is performed, and (S10) a step of determining presence/absence or an amount of the target substance in the sample based on a result of the measurement.

The steps (S1) to (S4) and the steps (S6) to (S8) can be performed by the same methods as those in the steps (S1) to (S4) and the steps (S6) to (S8) in the embodiment in FIG. 8.

For example, in the analysis method of the embodiment, after the irradiation of the excitation light in the step (S4) and the step (S8) is performed, the irradiation of the excitation light is stopped in the step (S4-2) and the step (S8-2) respectively, and then, the step (S5) and the step (S9) are performed after standing for a predetermined time respectively.

In a case where the lanthanoid complex is used as the fluorescent dye, for example, the standing time can be set to 200 to 600 µsec, and in a case where the quantum dot is used as the fluorescent dye, for example, the standing time can be set to 10 to 20 nsec.

As a result, even when there is nonspecific adsorption of the impurities at the time when the measurement is performed in the step (S5) and the step (S9), the autofluorescence derived from the impurities is quenched, and thus, it is possible to measure the change of the $I_{sd}$ by the FRET derived from the fluorescent dyes labeled.

A relationship between an attenuation of the fluorescence intensity and a time after the excitation light is quenched is unambiguously determined if the fluorescent dye is determined. Therefore, if the standing time until the source-drain current is measured after the excitation light is quenched is determined, it is possible to obtain the amount of existence of the target substance, similarly to the case of the embodiment of FIG. 8. That is, a competitive state between the competing substance and the target substance in binding to the binding to the capturing body can be obtained from the amount of change of the source-drain currents before the irradiation of the excitation light and after a predetermined time elapses after the irradiation and the quenching of the excitation light.

According to the chemical sensor kit and the analysis method, the chemical sensor kit and the analysis method are hardly affected by impurities, and it is possible to accurately detect and quantify the target substance. That is, even if the impurities are nonspecifically adsorbed to the channel 3, influences of the absorption do not appear unless the impurities are miraculously the lanthanoid complex or the quantum dot. In addition, even when the fluorescence substances as described above are mixed as the impurities, if the sample is fluorescently observed in advance, it is possible to detect the contamination thereof.

In still another embodiment, the analysis method may be performed using the gate electrode. For example, the chemical sensor used in such an analysis method may be configured to form a graphene field effect transistor (graphene FET) structure with the gate electrode integrated with or separated from the chemical sensor when used.

Figure 19:
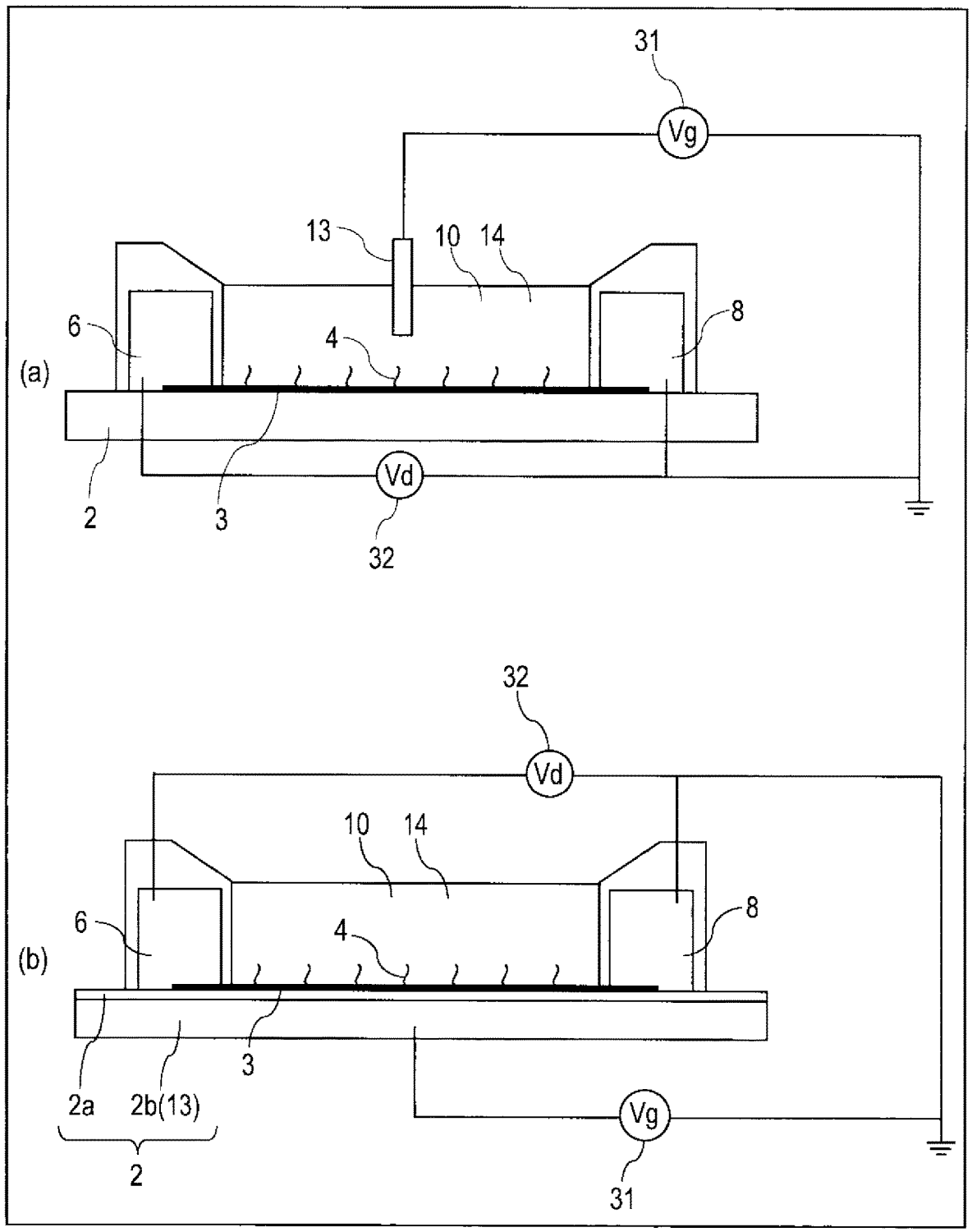
FIG. 19 shows sectional diagrams of the example of the analysis method of the embodiment.

FIG. 19 show an example of the state when the chemical sensor 1 used in the analysis method using the gate electrode. In this example, the chemical sensor 1 is the chemical sensor shown in FIG. 1. As shown in part (a) of FIG. 19, for example, a gate electrode 13 is disposed so as to come into contact with a solution 14 above the channel 3, that is, the reagent solution or the mixture solution of the sample and the reagent. The gate electrode 13 is connected to a power supply 31 and is configured to apply the gate voltage $V_g$ to the channel 3 via the solution 14. The source electrode 6 and the drain electrode 8 are connected to a power supply 32, and if the source-drain voltage ($V_{sd}$) is applied from the power supply, the source-drain current $I_{sd}$ flows from the source electrode 6 to the drain electrode 8 via the channel 3. The gate electrode 13 may be configured to be integrated with the chemical sensor 1 or may be configured to be separated from the chemical sensor 1.

Alternatively, the gate electrode 13 may be disposed in a back gate format. In this case, for example, as shown in part (b) of FIG. 19, it is preferable that the substrate 2 is configured to include an insulating film 2a provided on a surface of the channel side and a conductor 2b. It is preferable that a thickness of the insulating film 2a is as thin as possible within a range which does not impair the insulation properties, and for example, it is preferable that the thickness is approximately several nanometers. Here, the conductor 2b functions as the gate electrode 13. In this structure, the gate voltage $V_g$ is applied to the channel 3 via the insulating film 2a. For example, a circuit connecting these members to each other may be formed in the substrate 2.

The chemical sensor kit may include a gate electrode 13 which is integrated with or separated from the chemical sensor 1.

In the analysis method using the gate electrode, a constant gate voltage may be applied or fixed at 0 V, or a plurality of gate voltages may be applied for the measurement in the steps (S3), (S5), (S7), and (S9).

By applying the gate voltage ($V_g$), it is possible to measure the $I_{sd}$ using a portion having the $V_g$-$I_{sd}$ characteristics with high linearity. Alternatively, by measuring the $I_{sd}$ by applying a plurality of gate voltages, it is possible to obtain a voltage shift amount and inclination information of the $V_g$-$I_{sd}$ characteristics, and thus, it is possible to more accurately perform an interpretation and calculation processing of a measurement result.

Second Embodiment

In a chemical sensor kit according to a second embodiment, instead of the capturing body of the chemical sensor kit of the first embodiment, an unlabeled competing substance is fixed to a channel, and a reagent contains a capturing body labeled with a fluorescent dye instead of the competing substance. This second embodiment is the same as the first embodiment except that the disposition of the capturing body and the competing substance is different from that of the first embodiment. In addition, other configurations may be similar to those of the chemical sensor according to the first embodiment.

Figure 20:
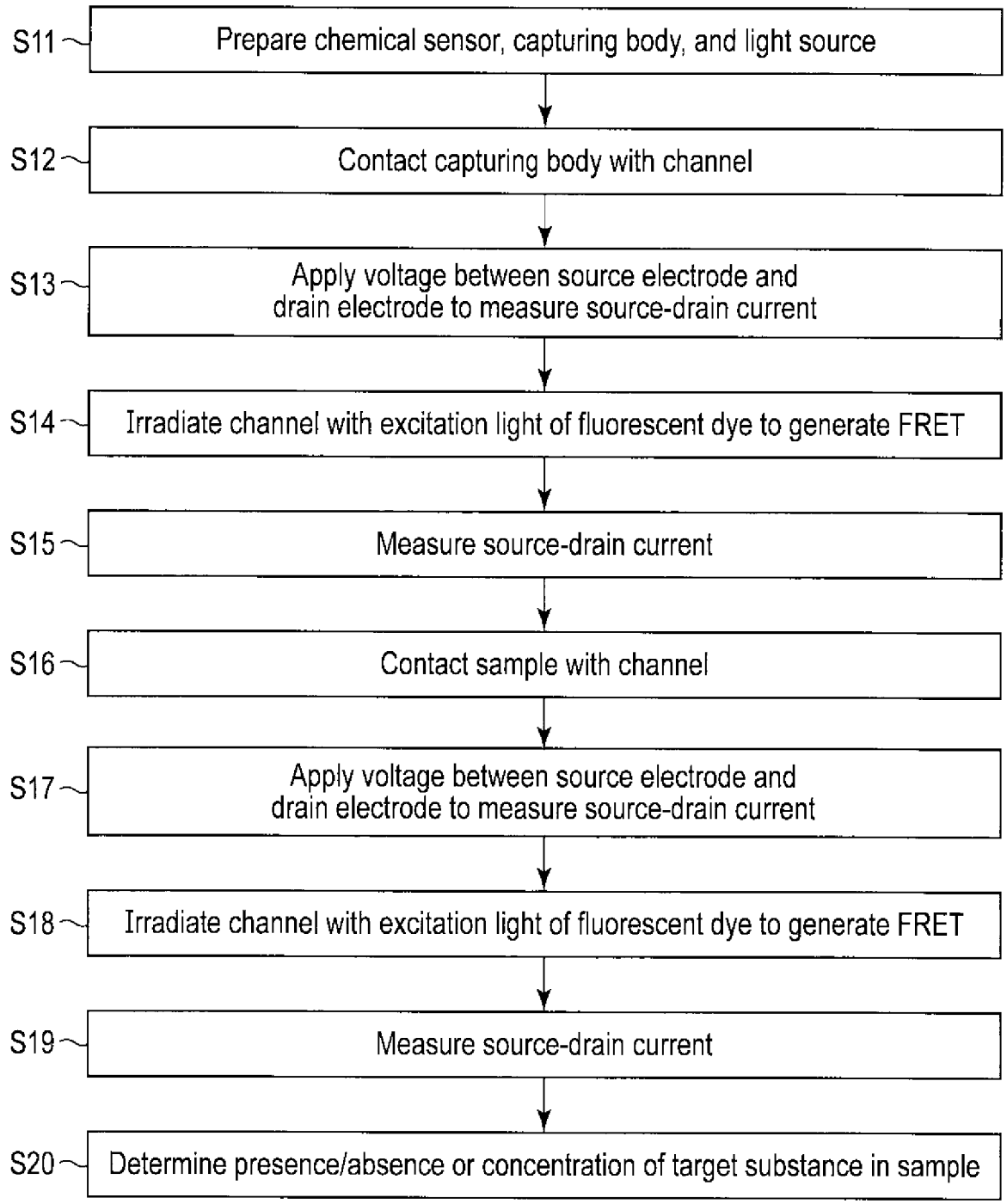
FIG. 20 shows a flowchart of an example of an analysis method of an embodiment.

An analysis method according to the second embodiment is shown in FIG. 20. A basic flow is the same as in the case of the first embodiment shown in FIG. 8. However, in the second embodiment, the competing substance and the capturing body are replaced by each other.

Figure 22:
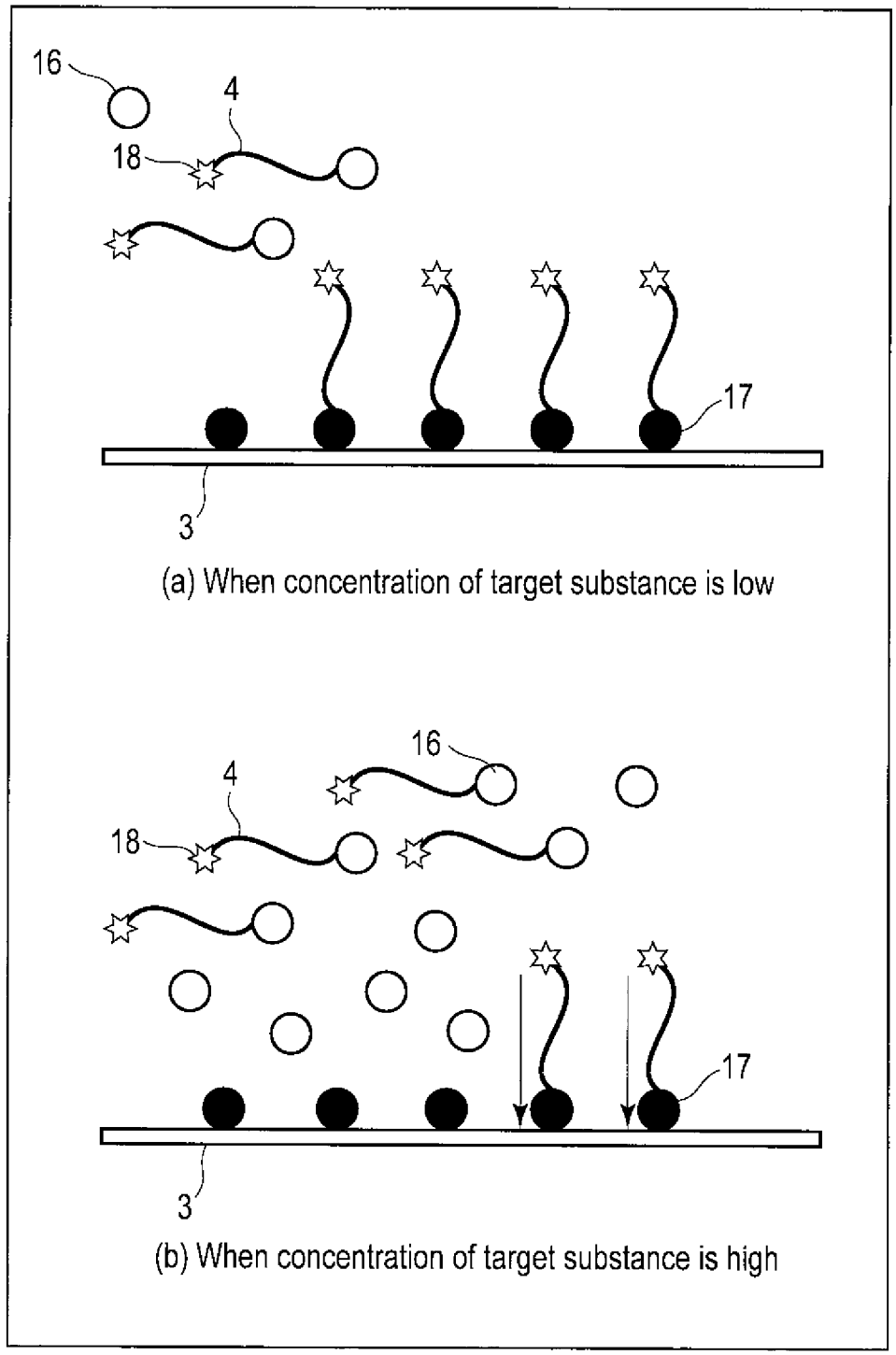
FIG. 22 shows enlarged diagrams of the state when the chemical sensor of the embodiment is used.
Figure 23:
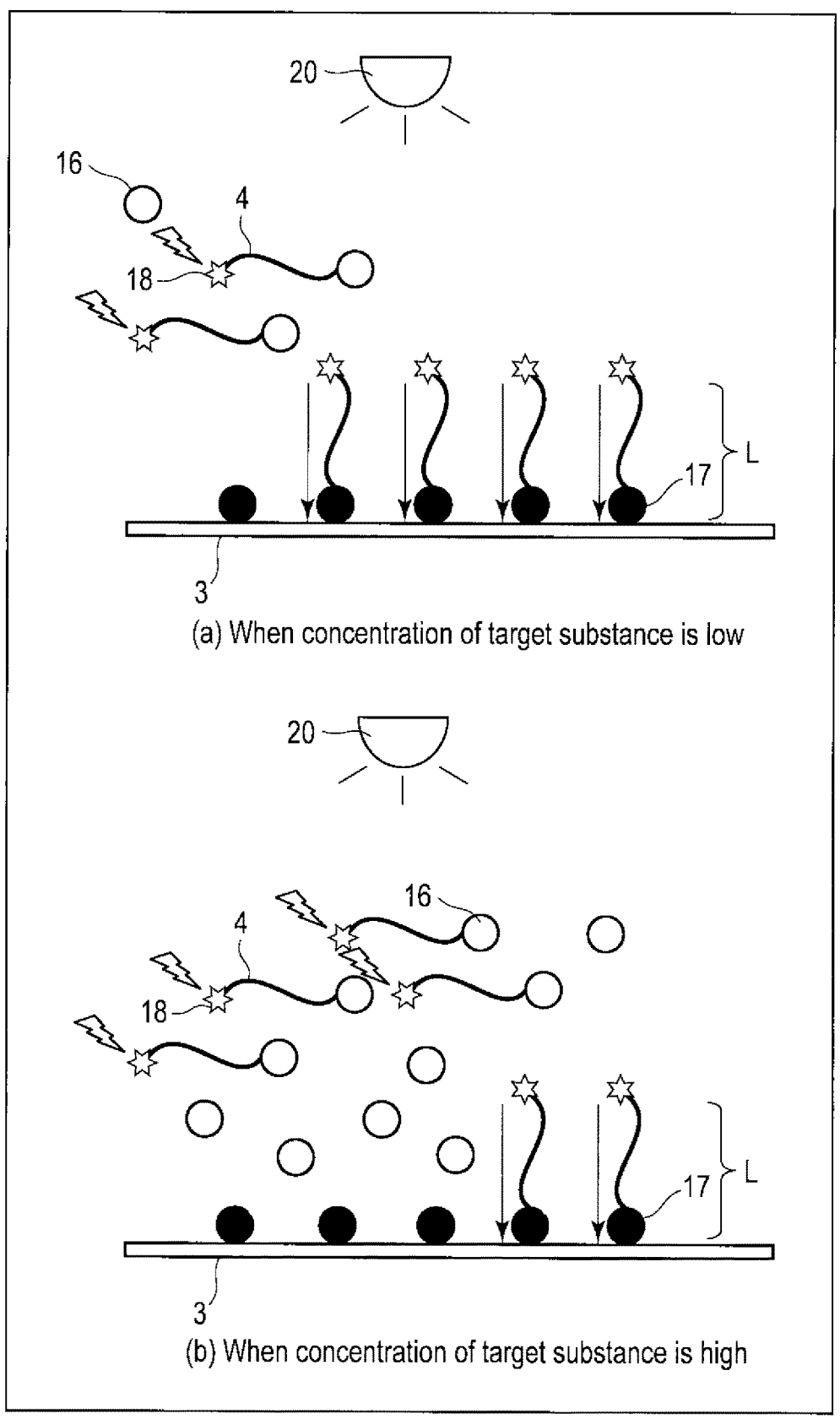
FIG. 23 shows enlarged diagrams of the state when the chemical sensor of the embodiment is used.

FIGS. 21 to 23 show behaviors of a fluorescently labeled capturing body, a sample, and a competing substance in the analysis method using the chemical sensor kit of the second embodiment and these FIGS corresponds to FIGS. 9, 12, and 13. FIG. 21 is enlarged diagrams of a channel 3 when fluorescently labeled capturing body comes into contact with the channel 3. As shown in part (a) of FIG. 21, capturing bodies 4 labeled with fluorescent dyes 18 bind to almost all of competing substances 17 fixed to the channel 3. As shown in part (b) of FIG. 21, if irradiation of the excitation light of the fluorescent dye 18 is applied, a fluorescence 19 is generated from the fluorescent dye 18, and the energy transfer by the FRET is generated between the channel 3 and the fluorescent dye 18 of the capturing body 4 binding to the competing substance 17 fixed to the channel 3.

FIG. 22 shows a state where the sample containing the target substance 16 is added on the channel in the step (S16). When the amount of the target substances 16 is small or concentrations thereof are low, as shown in part (a) of FIG. 22, the target substances 16 competitively deprive a few of the capturing bodies 4 that was bound to the competing substance 17 and bind to the deprived capturing bodies 4. On the other hand, when the amount of the target substances 16 is large or concentrations thereof are high, as shown in part (b) of FIG. 22, a ratio of the capturing bodies 4 deprived from the competing substances 17 increases. Therefore, as shown in FIG. 23, by applying the irradiation of the excitation light of the fluorescent dye 18 binding to the capturing body 4, the ratio of the capturing bodies 4 deprived from the competing substances 17, which is the difference of the amounts of existence of the target substances 16 in the sample, can be measured as the difference of the amount of energy transfer by the FRET (arrows in the drawings) to the channel 3.

The detection of the $I_{sd}$ and the presence/absence or the amount of the target substances can be performed by the same method as that of the first embodiment.

From the above-described configurations, according to the chemical sensor kit and the analysis method of the second embodiment, the detection results are hardly affected by the impurities contained in the sample and compositions of the sample or fluctuations of pH thereof, and it is possible to accurately detect or quantify the target substance.

Figure 24:
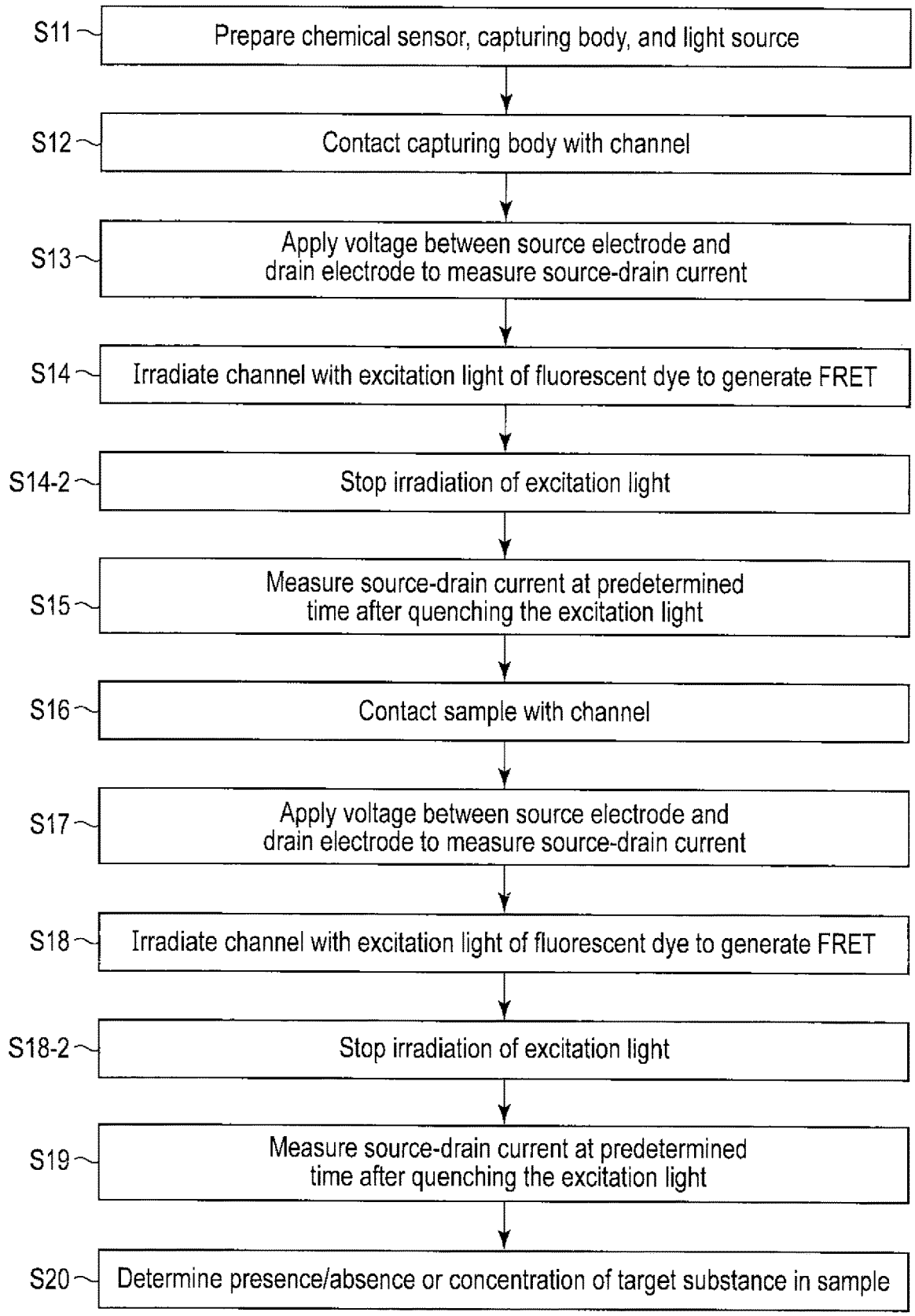
FIG. 24 shows a flowchart of an example of an analysis method of an embodiment.

Similarly to the first embodiment, in the second embodiment, the TR-FRET can be used by using a fluorescent dye having a fluorescence lifetime of 10 nsec or more as the fluorescent dye 18. In this case, the analysis method is similar to the case of the first embodiment shown in FIG. 18. However, in this embodiment, the competing substance and the capturing body are replaced by each other (FIG. 24). In this case, it is possible to prevent the energy transfer derived from the impurities from being detected, the selection of the blocking agent is facilitated, and it is possible to more accurately detect or quantify the target substance.

Third Embodiment

In a chemical sensor kit of a third embodiment, a second capturing body is used instead of the competing substance of the first embodiment. That is, in the chemical sensor kit of the third embodiment, a first capturing body is fixed to a channel, and a second capturing body which is labeled with a fluorescent dye and has a specific binding ability to a target substance is contained in a reagent. Other configurations may be similar to those of the chemical sensor of the first embodiment.

The second capturing body binds to a site of the target substance different from a site of the target substance to which the first capturing body binds. The first capturing body and the second capturing body can be any of the above capturing bodies. For example, the first capturing body may be a primary antibody and the second capturing body may be a secondary antibody.

Figure 25:
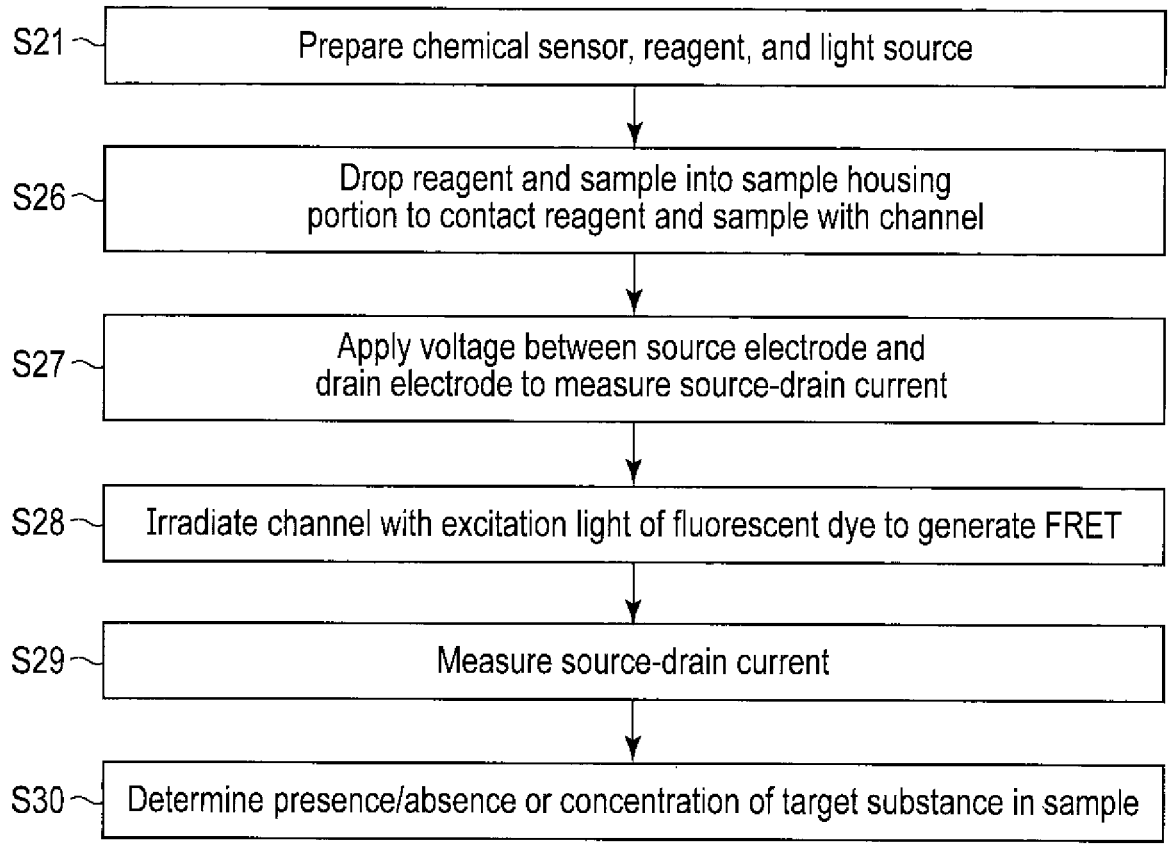
FIG. 25 shows a flowchart of an example of an analysis method of an embodiment.

An example of the analysis method according to the third embodiment is shown in FIG. 25. Unlike the first and second embodiment, in the third embodiment, since FRET is not generated when the target substance does not exist, it is not necessary to measure the FRET by only the reagent before a sample is supplied. Accordingly, steps are as follows.

First, in a step (S21), the chemical sensor and the reagent of the third embodiment, and a light source are prepared.

Next, in a step (S26), a sample accommodation portion is provided together with the reagent and the sample to come into contact with the channel. Here, in a case where both the reagent and the sample are solutions, the reagent and the sample can be sequentially dropped or can be mixed and dropped. In a case where the sample is a gas, it is possible to expose a gas containing a target gas to the sample accommodation portion to which the reagent solution is dropped.

Next, in a step (S27), a voltage is applied between a source electrode and a drain electrode and a source-drain current is measured.

Then, in a step (S28), irradiation of excitation light of the fluorescent dye binding to the second capturing body of the reagent is applied. At this time, if the target substance exists in the sample, via the target substance, the second capturing body binds to the first capturing body fixed to a channel 3 in a sandwich state, and thus, the FRET is generated from the fluorescent dye labeled to the second capturing body to the channel 3.

Next, in a step (S29), the source-drain current is measured in a state where the FRET is generated.

Next, in a step (S30), the presence/absence or the concentration of the target substance in the sample are determined.

Figure 26:
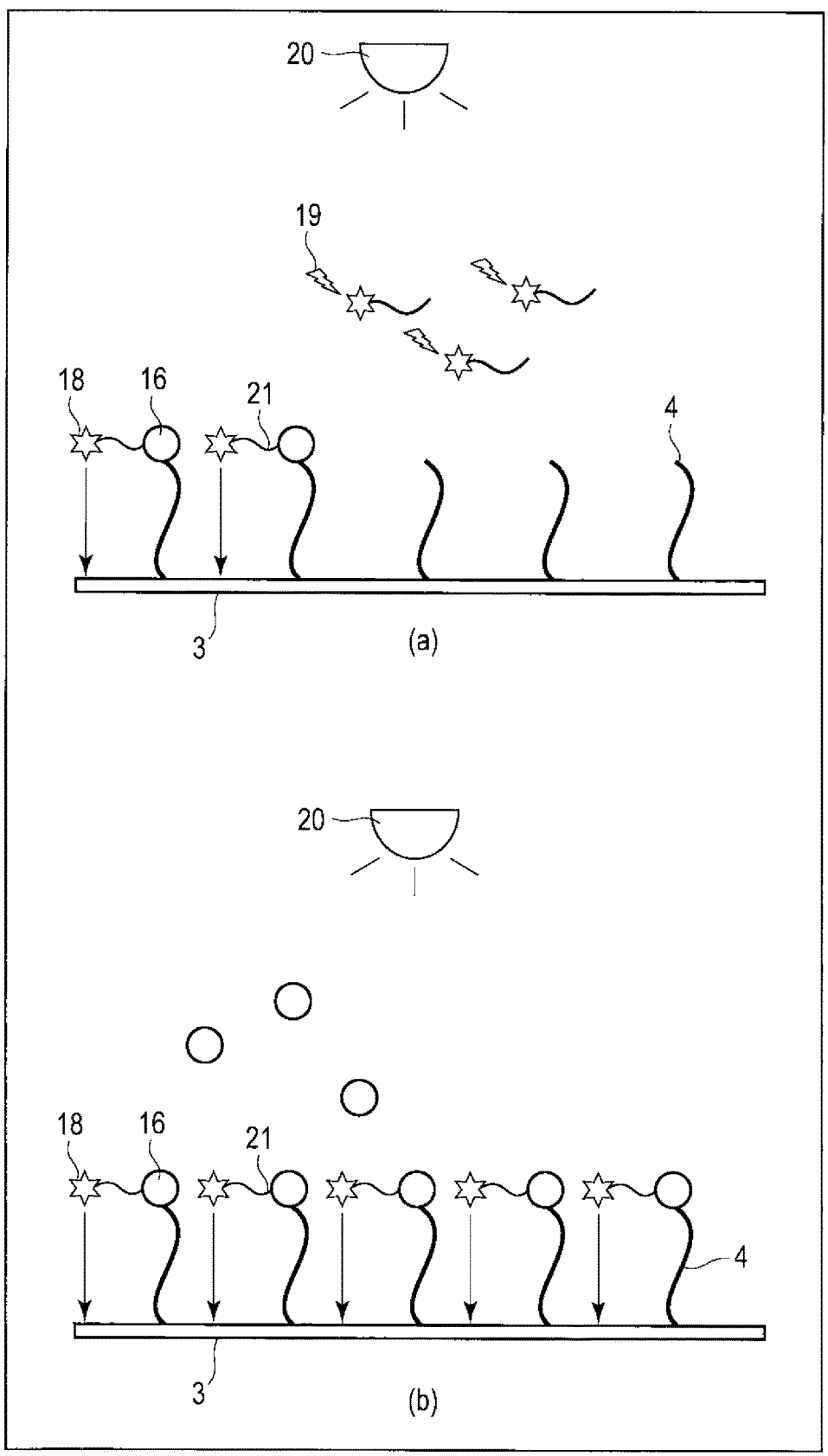
FIG. 26 shows an enlarged diagram of the state when the chemical sensor of the embodiment is used.

In the analysis method of the third embodiment, behaviors of constituent components when the sample and the fluorescently labeled second capturing body contact with the channel 3 will be described with reference to FIG. 26. FIG. 26 is enlarged diagrams of the channel 3. The sample and the fluorescently labeled second capturing body come into contact with the channel 3, and thus, a target substance 16 contained in the sample binds to a first capturing body 4 fixed to the channel 3, and a second capturing body 21 binds to the target substance 16.

In a case where the amount of existence of the target substance 16 is small (part (a) of FIG. 26), according to this, the amount of the second capturing body binding to the target substance 16 decreases, and a fluorescent dye 18 generating the FRET (arrow in part (a) of FIG. 26) decreases. In the opposite case (part (b) of FIG. 26), the fluorescent dye 18 generating the FRET increases. Accordingly, as the target substances 16 increases, the change of the $I_{sd}$ increases.

Figure 27:
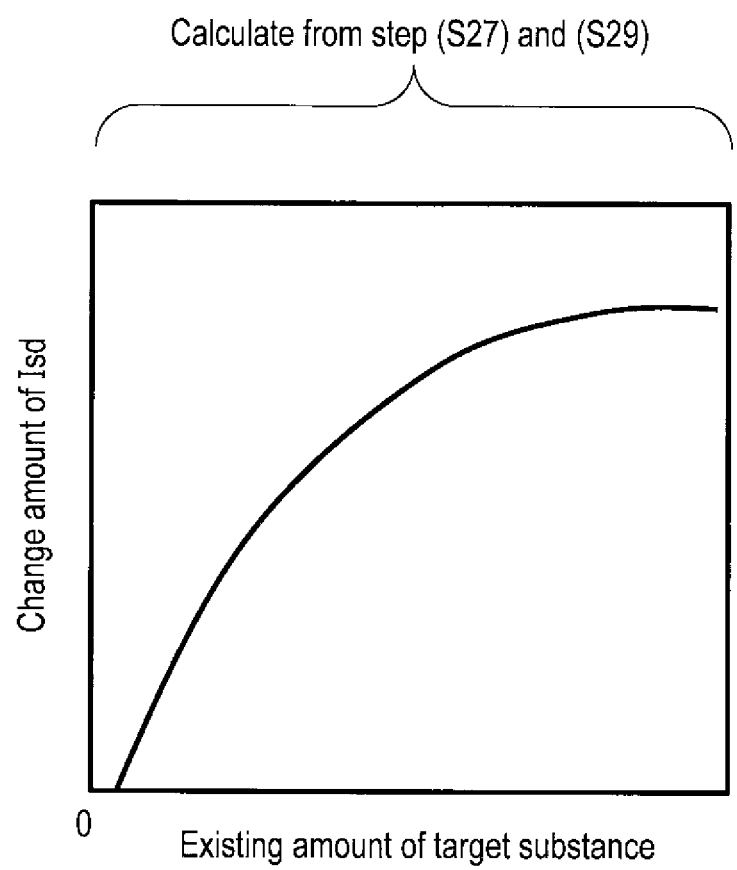
FIG. 27 shows graphs of an example of a relationship between an amount of change of the $I_{sd}$ and an amount of existence of a target substance.

FIG. 27 shows an example of a relationship between the amount of existence of the target substance and the amount of change of the source-drain current ($I_{sd}$) by the FRET. The amount of change of the $I_{sd}$ by the FRET can be obtained from a difference between the $I_{sd}$ measured in the step (S27) and the $I_{sd}$ measured in the step (S29) In a case where the $I_{sd}$s of the steps (S27) and (S29) are the same or there is no significant difference therebetween, it can be determined that "the target substance does not exist in the sample or the target substance exists only equal to or less than a detection limit". In a case where the $I_{sd}$'s in steps (S27) and (S29) are significantly different from each other, it can be determined that "the target substance exists in the sample".

Alternatively, the amount of the target substance may be determined from the amount of change of the $I_{sd}$. For example, the determination of the amount of the target substance may be performed by preparing a calibration curve.

From the above-described configurations, according to the chemical sensor kit and the analysis method of the third embodiment, the detection results are hardly affected by the impurities contained in the sample and compositions of the sample or fluctuations of pH thereof, the blocking agent is easily selected, and it is possible to accurately detect or quantify the target substance.

Figure 28:
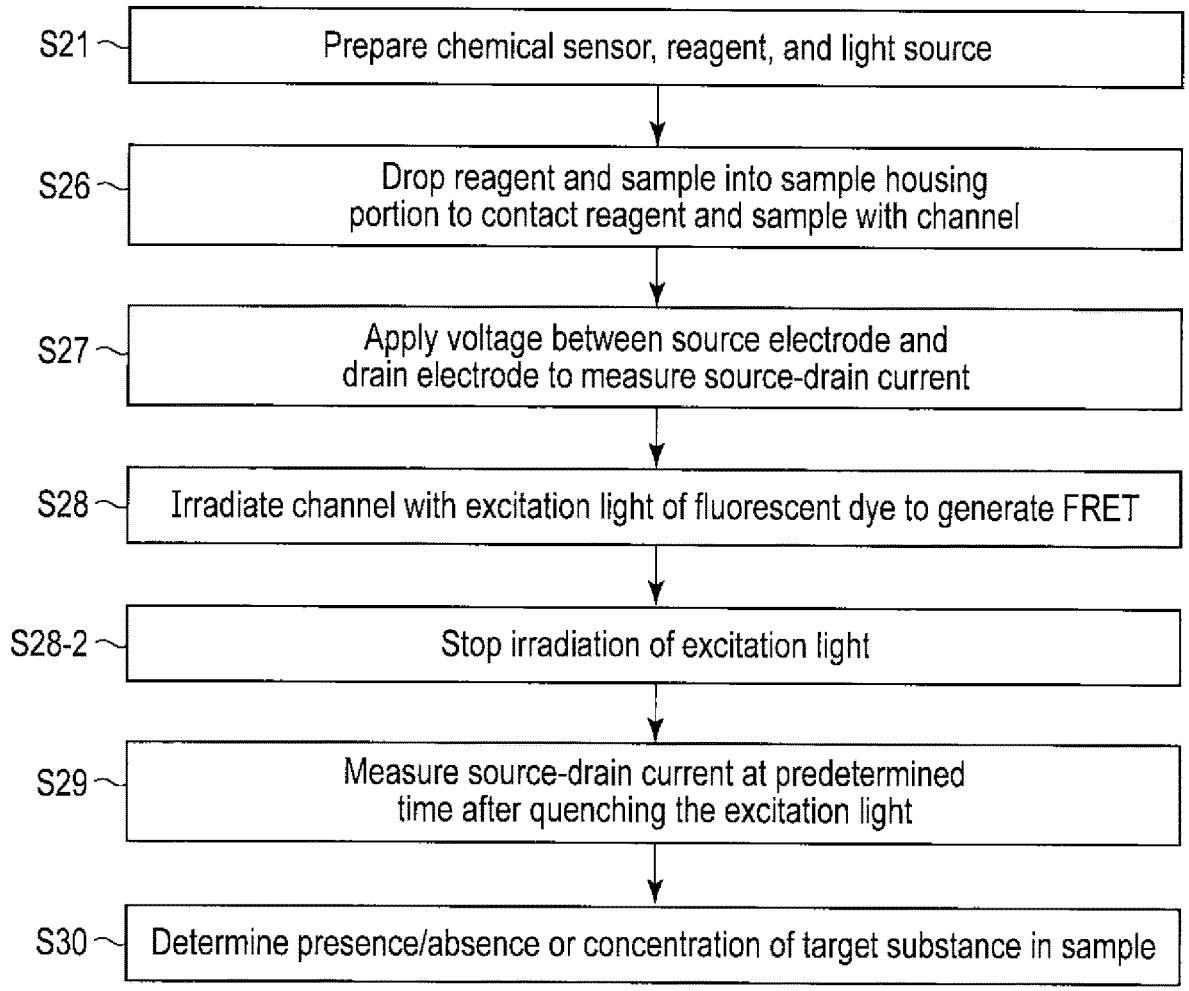
FIG. 28 shows a flowchart of an example of an example of an analysis method of an embodiment.

Similarly to the first embodiment, in the third embodiment, TR-FRET can be used by using a fluorescent dye having a fluorescence lifetime of 10 nsec or more. An analysis method in this case is shown in FIG. 28. After the step (S28) and before the step (S29), a step (S28-2) of stopping the irradiation of the excitation light is provided. In this case, it is possible to prevent the energy transfer derived from the impurities from being detected, and it is possible to more accurately detect or quantify the target substance.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A chemical sensor kit comprising:
    a chemical sensor which includes
        a substrate,
        a channel which is disposed on a surface of the substrate and includes a hexagonal crystal lattice composed of carbon atoms,
        a source electrode which is connected to one end of the channel,
        a drain electrode which is connected to another end of the channel, and
        a first substance fixed to the channel; and
    a reagent which contains a second substance labeled with a fluorescent dye,
    wherein one of the first substance and the second substance is a capturing body which is an antibody, antigen binding fragment, or oligopeptide and has a specific binding ability to a target substance in a sample, and the other one is a competing substance which has a binding ability to the capturing body and competes with the target substance for the binding to the capturing body.

2. The chemical sensor kit of claim 1, wherein the channel is a graphene or carbon nanotube.

3. The chemical sensor kit of claim 1, wherein the fluorescent dye is a europium complex or a quantum dot.

4. The chemical sensor kit of claim 1, wherein the surface of the channel to which the first substance is fixed is covered with a blocking agent.

5. A chemical sensor kit comprising:
    a chemical sensor which includes
        a substrate,
        a channel which is disposed on a surface of the substrate and includes a hexagonal crystal lattice composed of carbon atoms,
        a source electrode which is connected to one end of the channel,
        a drain electrode which is connected to another end of the channel, and
        a first substance fixed to the channel; and
    a reagent which contains a second substance labeled with a fluorescent dye, wherein
    the first substance is a first capturing body which has a specific binding ability to a target substance in a sample, and the second substance is a second capturing body which has a specific binding ability to the target substance, and
    the first capturing body and the second capturing body bind to different sites of the target substance.

6. The chemical sensor kit of claim 5, wherein the channel is a graphene or carbon nanotube.

7. The chemical sensor kit of claim 5, wherein the fluorescent dye is a europium complex or a quantum dot.

8. The chemical sensor kit of claim 5, wherein the capturing body is an antibody, antigen binding fragment, oligopeptide, or an aptamer.

9. The chemical sensor kit of claim 5, wherein the surface of the channel to which the first substance is fixed is covered with a blocking agent.

10. An analysis method comprising:
    (i) preparing
        a chemical sensor which includes
            a substrate,
            a channel which is disposed on a surface of the substrate and includes a hexagonal crystal lattice composed of carbon atoms, and
            a capturing body which has a specific binding ability to a target substance in a sample and is fixed to the channel; and
        a competing substance which is labeled with a fluorescent dye, has a binding ability to the capturing body, and competes with the target substance for the binding to the capturing body;
    (ii) bringing the competing substance into contact with the channel;
    (iii) bringing the sample into contact with the channel;
    (iv) applying a DC voltage to the channel to measure a current flowing through the channel as first measurement;
    (v) irradiating the channel with excitation light of the fluorescent dye to excite the fluorescent dye thereby transferring excitation energy of the fluorescent dye labeling the competing substance bound with the capturing body to the channel;
    (vi) applying a DC voltage to the channel to measure a current flowing through the channel as second measurement; and
    (vii) determining a presence/absence or an amount of the target substance based on results of the first measurement and the second measurement.

11. The analysis method of claim 10, further comprising: between (ii) and (iii), (ii-1) applying a DC voltage to the channel to measure a current flowing through the channel as third measurement;
(ii-2) irradiating the channel with excitation light of the fluorescent dye to excite the fluorescent dye thereby transferring the excitation energy of the fluorescent dye labeling the competing substance bound with the capturing body to the channel; and
(ii-3) applying a DC voltage to the channel to measure a current flowing through the channel as fourth measurement.

12. The method of claim 10, further comprising:
(v-1) stopping irradiation of the excitation light after (v) and before (vi), wherein (vi) is performed after standing for a predetermined time after (v-1).

13. The method of claim 10, further comprising:
(v-1) stopping irradiation of the excitation light after (v) and before (vi), wherein (vi) is performed after standing for a predetermined time after (v-1); and
(ii-2-1) stopping irradiation of the excitation light after (ii-2) and before (ii-3), wherein (ii-3) is performed after waiting for a predetermined time after (ii-2-1).

14. An analysis method comprising:
(i) preparing
   a capturing body which is labeled with a fluorescent dye and has a specific binding ability to a target substance in a sample; and
   a chemical sensor which includes
      a substrate,
      a channel which is disposed on a surface of the substrate and contains a hexagonal crystal lattice composed of carbon atoms, and
      a competing substance which has a binding ability to the capturing body and competes with the target substance in binding to the capturing body being fixed to the channel;
(ii) bringing the capturing body into contact with the channel;
(iii) bringing the sample into contact with the channel;
(iv) applying a DC voltage to the channel to measure a current flowing through the channel as first measurement;
(v) irradiating the channel with excitation light of the fluorescent dye to excite the fluorescent dye thereby transferring excitation energy of the fluorescent dye labeling the capturing body bound with the competing substance to the channel;
(vi) applying a DC voltage to the channel to measure a current flowing through the channel as second measurement; and
(vii) determining a presence/absence or an amount of the target substance based on results of the first measurement and the second measurement.

15. The analysis method of claim 14, further comprising: between (ii) and (iii),
(ii-1) applying a DC voltage to the channel to measure a current flowing through the channel as third measurement;
(ii-2) irradiating the channel with excitation light of the fluorescent dye to excite the fluorescent dye thereby transferring excitation energy of the fluorescent dye labeling the capturing body bound with the competing substance to the channel; and
(ii-3) applying a DC voltage to the channel to measure a current flowing through the channel as fourth measurement.

16. The method of claim 14, further comprising:
(v-1) stopping irradiation of the excitation light after (v) and before (vi), wherein (vi) is performed after standing for a predetermined time after (v-1).

17. The method of claim 15, further comprising:
(v-1) stopping irradiation of the excitation light after (v) and before (vi), wherein (vi) is performed after standing for a predetermined time after (v-1); and
(ii-2-1) stopping irradiation of the excitation light after (ii-2) and before (ii-3), wherein (ii-3) is performed after waiting for a predetermined time after (ii-2-1).

18. An analysis method comprising:
(i) preparing
   a chemical sensor which includes
      a substrate,
      a channel which is disposed on a surface of the substrate and includes a hexagonal crystal lattice composed of carbon atoms, and
      a first capturing body which has a specific binding ability to a target substance in a sample being fixed to the channel; and
   a second capturing body which is labeled with a fluorescent dye and has a specific binding ability to the target substance;
(ii) bringing the second capturing body into contact with the channel;
(iii) bringing the sample into contact with the channel;
(iv) applying a DC voltage to the channel to measure a current flowing through the channel as first measurement;
(v) irradiating the channel with excitation light of the fluorescent dye to excite the fluorescent dye thereby transferring excitation energy of the fluorescent dye labeling the second capturing body bound with the first capturing body together with the target substance, to the channel;
(vi) applying a DC voltage to the channel to measure a current flowing through the channel as second measurement; and
(vii) determining a presence/absence or an amount of the target substance in the sample based on results of the first measurement and the second measurement.

19. The method of claim 18, further comprising:
(v-1) stopping irradiation of the excitation light after (v) and before (vi), wherein (vi) is performed after standing for a predetermined time after (v-1).

* * * * *